(12) United States Patent
Yang et al.

(10) Patent No.: US 7,898,005 B2
(45) Date of Patent: Mar. 1, 2011

(54) INORGANIC NANOTUBES AND ELECTRO-FLUIDIC DEVICES FABRICATED THEREFROM

(75) Inventors: Peidong Yang, Kensington, CA (US); Arunava Majumdar, Orinda, CA (US); Rong Fan, Pasadena, CA (US); Rohit Karnik, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 68 days.

(21) Appl. No.: 12/335,430

(22) Filed: Dec. 15, 2008

(65) Prior Publication Data
US 2009/0283751 A1    Nov. 19, 2009

Related U.S. Application Data

(60) Continuation of application No. PCT/US2007/071300, filed on Jun. 15, 2007, and a continuation-in-part of application No. 11/969,010, filed on Jan. 3, 2008, which is a continuation of application No. PCT/US2006/026318, filed on Jul. 6, 2006, and a continuation-in-part of application No. 12/027,428, filed on Feb. 7, 2008, which is a division of application No. 10/822,148, filed on Apr. 8, 2004, now Pat. No. 7,355,216, and a continuation-in-part of application No. 10/731,745, filed on Dec. 8, 2003, now Pat. No. 7,211,143.

(60) Provisional application No. 60/814,264, filed on Jun. 15, 2006, provisional application No. 60/697,332, filed on Jul. 6, 2005, provisional application No. 60/461,346, filed on Apr. 8, 2003, provisional application No. 60/461,346, filed on Apr. 8, 2003, provisional application No. 60/454,038, filed on Mar. 11, 2003, provisional application No. 60/432,104, filed on Dec. 9, 2002.

(51) Int. Cl.
*G01N 27/447* (2006.01)
(52) U.S. Cl. .................. 257/200; 257/E21.108
(58) Field of Classification Search .............. 257/200, 257/E21.108
See application file for complete search history.

(56) References Cited

U.S. PATENT DOCUMENTS 5,352,512 A    10/1994 Hoffman (Continued)

OTHER PUBLICATIONS

Ito et al., "Observation of DNA transport through a single carbon nanotube channel", Chem. Commun. 13, 1482 (2003).*

(Continued)

*Primary Examiner*—Thomas L Dickey
(74) *Attorney, Agent, or Firm*—John P. O'Banion

(57) ABSTRACT

Nanofluidic devices incorporating inorganic nanotubes fluidly coupled to channels or nanopores for supplying a fluid containing chemical or bio-chemical species are described. In one aspect, two channels are fluidly interconnected with a nanotube. Electrodes on opposing sides of the nanotube establish electrical contact with the fluid therein. A bias current is passed between the electrodes through the fluid, and current changes are detected to ascertain the passage of select molecules, such as DNA, through the nanotube. In another aspect, a gate electrode is located proximal the nanotube between the two electrodes thus forming a nanofluidic transistor. The voltage applied to the gate controls the passage of ionic species through the nanotube selected as either or both ionic polarities. In either of these aspects the nanotube can be modified, or functionalized, to control the selectivity of detection or passage.

23 Claims, 19 Drawing Sheets

U.S. PATENT DOCUMENTS

| | | | |
|---|---|---|---|
| 6,113,722 | A | 9/2000 | Hoffman et al. |
| 6,123,819 | A | 9/2000 | Peeters |
| 6,194,066 | B1 | 2/2001 | Hoffman |
| 6,221,154 | B1 | 4/2001 | Lee et al. |
| 6,413,880 | B1 | 7/2002 | Baski et al. |
| 6,613,875 | B1 | 9/2003 | Ghadiri |
| 6,656,573 | B2 | 12/2003 | Chen et al. |
| 6,962,823 | B2 | 11/2005 | Empedocles et al. |
| 7,077,939 | B1 * | 7/2006 | Crooks et al. ............ 204/450 |
| 2002/0117659 | A1 | 8/2002 | Lieber et al. |
| 2002/0130311 | A1 | 9/2002 | Lieber et al. |
| 2002/0175408 | A1 | 11/2002 | Majumdar et al. |
| 2003/0127329 | A1 * | 7/2003 | DeVoe et al. ............ 204/454 |
| 2003/0165418 | A1 | 9/2003 | Ajayan et al. |
| 2004/0005723 | A1 | 1/2004 | Empedocles et al. |
| 2004/0076681 | A1 | 4/2004 | Dennis et al. |
| 2004/0124084 | A1 | 7/2004 | Lee et al. |
| 2004/0175844 | A1 | 9/2004 | Yang et al. |
| 2004/0235016 | A1 | 11/2004 | Hamers et al. |
| 2004/0262636 | A1 | 12/2004 | Yang et al. |
| 2005/0024433 | A1 | 2/2005 | Cruz-Uribe et al. |
| 2005/0036939 | A1 | 2/2005 | Wong et al. |
| 2005/0053525 | A1 | 3/2005 | Segal et al. |
| 2005/0056118 | A1 | 3/2005 | Xia et al. |
| 2005/0101020 | A1 | 5/2005 | Salem et al. |

OTHER PUBLICATIONS

Sun et al.,"Single Carbon Nanotube Membranes: A Well-Defined Model for Studying Mass Transport", J. Am. Chem. Soc., 2000, 122 (49), pp. 12340-12345.*

Cao et al. "Fabrication of 10 nm enclosed nanofluidic channels" Appl. Phys. Letter, vol. 81, No. 1, pp. 174-176 (2002).

Chen et al. "Preparation and characterization of carbon nanotubes encapsulated GaN nanowires" J. Phys. Chem Solids, vol. 62, pp. 1577-1586 (2001).

Kang et al. "Investigations of potential-dependent fluxes of ionic permeates in gold nanotubule membranes prepared via the template method" Langmuir, vol. 17, No. 9, pp. 2753-2759 (2001).

Mayya et al. "Nanotubes prepared by templating sacrificial nickel nanorods" Nano Letters, vol. 2001, No. 12, pp. 727-730 (2001).

Nishizawa et al. "Metal nanotubule membranes with electrochemically switchable ion-transport selectivity" Science, vol. 268, pp. 700-702 (1995).

Satishkumar et al., "Oxide nanotubes prepare using carbon nanotubes as templates" J. Mater Res/. vol. 12, No. 3, pp. 604-606 (1997).

Schasfoort et al. "Field-effect flow control for microfabricated fluidic networks" Science, vol. 286, pp. 942-045 (1999).

Schmidt et al. "Free-standing SiGe-based nanopipelines on Si (0001) substrates" Appl. Phys. Lett., vol. 78, No. 21, pp. 3310-3312 (2001).

Zhang et al. "Synthesis of coaxial nanotubes: Titanium oxide sheathed with silicon oxide" J. Mater. Res., vol. 16, No. 5, pp. 1408-1412 (2001).

Fan et al. "Polarity switching and transient responses in single nanotube nanofluidic transistors" Phys. Review Letters, vol. 95, issue 8, ID 086607 (Aug. 2005).

Fan et al. "DNA translocation in inorganic nanotubes" Nano Letters, vol. 5, No. 9, pp. 1663-1667 (2005).

Kamik et al. "Effects of biological reactions and modifications on conductance of nanofluidic channels" Nano Letters, vol. 5, No. 9, pp. 1638-1642 (2005).

Yang "Inorganic nanotubes, nanofluidic transistors and DNA translocation" Abstract for the Mar. 2006 Meeting of the American Physical Society, Mar. 13-17, 2006, Baltimore, MD.

Wu et al. "Heterostructures of ZnO-Zn coaxial nanocables and ZnO nanotubes" Appl. Phys. Letters, vol. 81, No. 7 pp. 1312-1314 (Aug. 12, 2002).

Mensah et al. "Formation of single crystalline ZnO nanotubes without catalysts and templates" Appl. Phys. Letters, vol. 90, pp. 113108-1-113108-3 (Mar. 12, 2007).

* cited by examiner

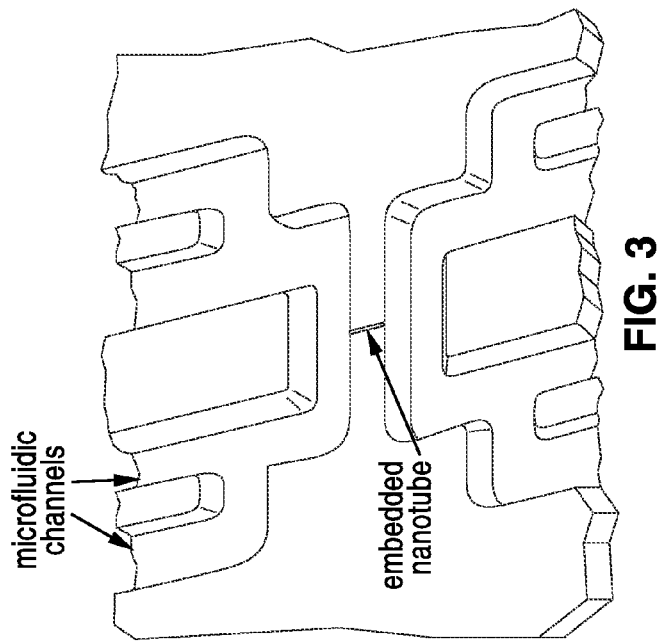
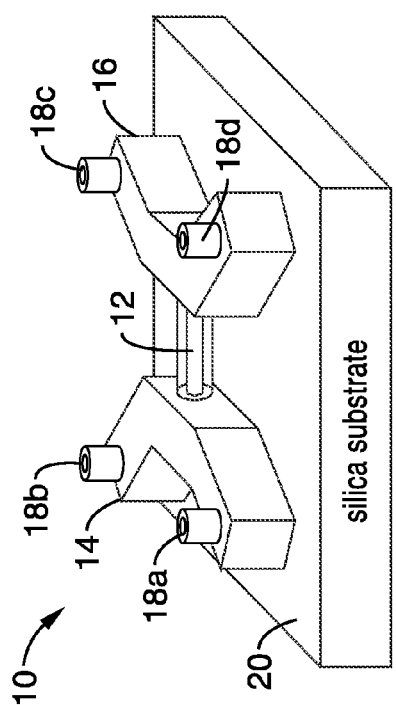
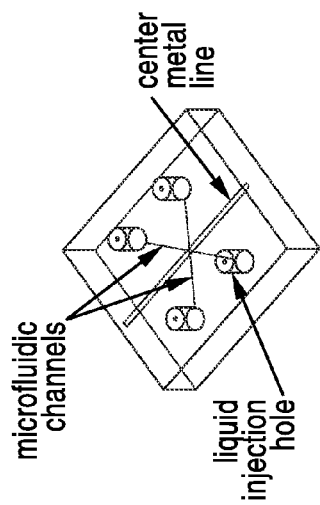

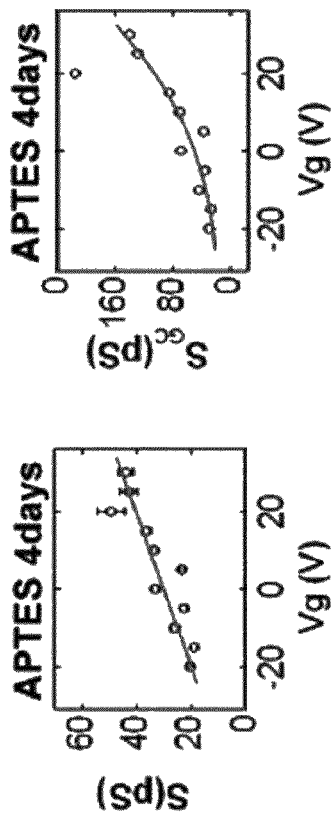
FIG. 21B
FIG. 21A
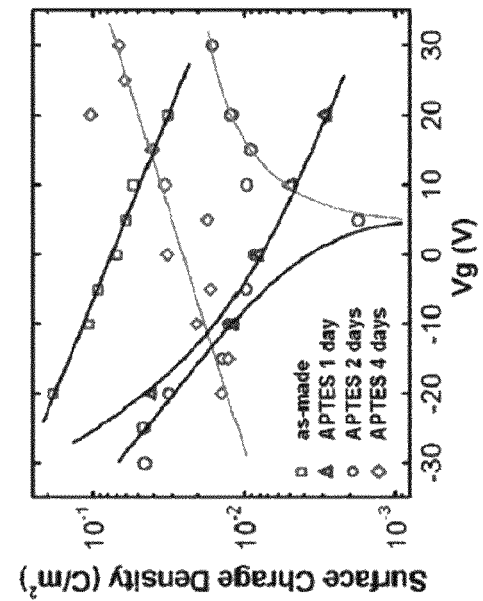
FIG. 23
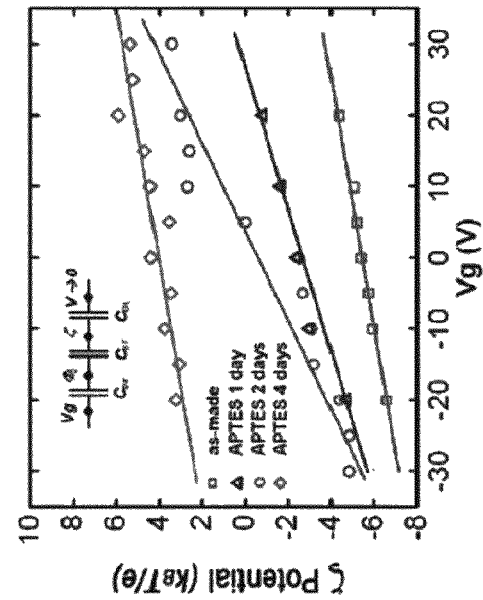
FIG. 22

(i) Deprotonation/protonation
(ii) Adsorption/desorption of cations
(iii) EF flow to reach steady states

INORGANIC NANOTUBES AND ELECTRO-FLUIDIC DEVICES FABRICATED THEREFROM

CROSS-REFERENCE TO RELATED APPLICATIONS (a) This application claims priority from, and is a 35 U.S.C. §111(a) continuation of, PCT international application serial number PCT/US2007/071300 filed on Jun. 15, 2007, which designates the U.S., incorporated herein by reference in its entirety, which claims priority from U.S. provisional application Ser. No. 60/814,264 filed on Jun. 15, 2006, incorporated herein by reference in its entirety; (b) This application is also a continuation in part of U.S. application Ser. No. 11/969,010 filed on Jan. 3, 2008, incorporated herein by reference in its entirety, which claims priority from, and is a 35 U.S.C. §111(a) continuation of, PCT international application serial number PCT/US2006/026318, filed on Jul. 6, 2006, incorporated herein by reference in its entirety, which in turn claims priority to U.S. provisional application Ser. No. 60/697,332 filed on Jul. 6, 2005, incorporated herein by reference in its entirety; (c) This application is also a continuation in part of U.S. application Ser. No. 12/027,428 filed on Feb. 7, 2008, which is a divisional of U.S. application Ser. No. 10/822,148 filed on Apr. 8, 2004, now U.S. Pat. No. 7,355,216, incorporated herein by reference in its entirety, and which claims priority to U.S. provisional application Ser. No. 60/461,346 filed on Apr. 8, 2003, incorporated herein by reference in its entirety, and which is also a continuation-in-part of U.S. application Ser. No. 10/731,745 filed on Dec. 8, 2003, now U.S. Pat. No. 7,211,143, incorporated herein by reference in its entirety, which claims priority to U.S. provisional application Ser. No. 60/461,346 filed on Apr. 8, 2003, incorporated herein by reference in its entirety, U.S. provisional application Ser. No. 60/454,038 filed on Mar. 11, 2003, incorporated herein by reference in its entirety, and U.S. provisional application Ser. No. 60/432,104 filed on Dec. 9, 2002, incorporated herein by reference in its entirety.

This application is related to, and incorporates herein by reference, each of the following disclosures in their entireties which also correspond to priority claims above: PCT International Publication No. WO 2008/039579 published on Apr. 3, 2008; PCT International Publication No. WO 2008/048209 published on Apr. 24, 2008; U.S. Pat. No. 7,211,143 issued on May 1, 2007; and U.S. Pat. No. 7,355,216 issued on Apr. 8, 2008.

STATEMENT REGARDING FEDERALLY SPONSORED RESEARCH OR DEVELOPMENT

This invention was made with Government support under Grant No. CA103071, awarded by the National Institutes of Health; and Grant No. DE-AC02-05CH11231, awarded by the Department of Energy. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to nanofluidic devices, and more particularly to electronic devices for fluidic sensing and control, including functionalized nanochannels providing modifiable channel geometry and ionic environment and devices fabricated therefrom.

2. Description of Related Art

In recent years microfluidics and nanofluidics have arisen as important technologies dealing with the behavior, precise detection, control and manipulation of microliter, nanoliter and even down to femtoliter volumes of fluids. Applications for microfluidics and nanofluidics are wide ranging and of increasing interest in the fields of chemistry, engineering, biotechnology (e.g., DNA, lab-on-a-chip), and so forth. Advances in microfluidics are revolutionizing molecular biology procedures for enzymatic analysis (e.g., glucose and lactate assays), DNA analysis (e.g., polymerase chain reaction and high-throughput sequencing), and proteomics. One of the important aspects of microfluidic biochip design is integrating assay operations such as detection, as well as sample pre-treatment and sample preparation on one chip.

Continued developments are arising in the area of DNA research with using microfluidics. Early biochips were largely based on the concept of a DNA microarray (e.g., the GeneChip DNAarray from Affymetrix) which is a piece of glass, plastic or silicon substrate on which pieces of DNA (probes) are affixed in a microscopic array. Protein arrays have been similarly configured with different capture agents used to determine the presence and/or amount of proteins contained in biological samples.

Increasingly, interest is being directed toward the nanofluidic realm. Nanofluidics is generally considered the study of the behavior, manipulation, and control of fluids that are confined to structures of nanometer (typically 1-100 nm) characteristic dimensions (1 nm=$10^{-9}$ m). The design of these structures often diverges from the microfluidic realm in that fluids confined in these structures exhibit physical behaviors not observed in larger structures as a consequence of the characteristic changes which arise as the physical scaling lengths of the fluid, (e.g., hydrodynamic radius and Debye length) begin to converge on the nanostructural dimensions.

A number of shortcomings exist with existing fluidic devices. Some of the drawbacks with existing devices relate to the transient nature of the testing (non-continuous) as well as the difficulty in registering results.

Accordingly, a need exists for nanofluidic device technology which can be run continuously while readily registering results. The nanofluidic devices according to the present invention fulfill those needs and others, while overcoming drawbacks of previous devices.

The detection and analysis of interactions between biological molecules is a significant area of research in the healthcare and biotechnology fields. Many molecular detection, analysis and separation techniques have been developed and validated in recent years. For most processes, efficiency is a result of a trade-off between sensitivity, specificity, ease of operation, cost, speed and avoidance of false positives. Typical biological sensing techniques require a series of preparation steps, a number of reagents and schemes to separate components, a relatively large sample size and complex data analysis.

Miniaturization and mechanization of biological sensing techniques can lower sample sizes, reduce the time and expense of the process and increase diagnostic sensitivity. Emerging micro- and nano-technologies can decrease the size, weight and cost of sensors and sensor arrays by orders of magnitude, and increase their spatial and temporal resolution and accuracy. Novel functional materials such as quantum dots, photonic crystals, nanowires, carbon nanotubes, porous membranes, porous silicon and sol-gel matrices incorporating biomolecules have been used as sensing elements with various possible detection mechanisms.

Hollow inorganic nanotubes are of particular interest due to their potential applications in bioanalysis and catalysis. For example, silica nanotubes are of special interest because of their hydrophilic nature, easy colloidal suspension formation, and surface functionalization accessibility for both inner and outer walls. Such modified silica nanotubes and nanotube membrane have shown potential applications for bioseparation and biocatalysis.

In addition, one-dimensional nanostructures (nanotubes and nanowires) have also made miniaturized chemical and biological sensing elements possible. The ultrahigh surface to volume ratios of these structures make their electrical properties extremely sensitive to surface-adsorbed species, as has been shown with carbon nanotubes, functionalized silicon nanowires and metal nanowires.

Chemical and biological nanosensors are advantageous because of their potential for detecting very low concentrations of biomolecules or pollutants on platforms small enough to be used in vivo or on a microchip. For example, a room temperature photochemical NO2 sensor has been demonstrated based on individual single-crystalline oxide nanowires and nanoribbons.

Chemical/sensing systems have also been developed using silica tubular membranes creating a new class of molecular sieves for molecular separation and electrochemical sensing based on the size of the molecules as well as interaction of the molecules with the surface functional groups of the tube. Normally, an inorganic nanotube membrane (polycarbonate or porous alumina) is set up to separate two salt solutions and a constant transmembrane potential is applied, then the transmembrane current is measured. When an analyte of comparable dimensions to the tube diameter is added to one of the solutions, a decrease in transmembrane current is sensed because of the current blocking by the molecules. Using such schemes, very small traces of different ions and molecules can be detected. These experiments, however, have all relied on using entire membranes as sensing elements. No significant efforts have been placed on single tube sensing, although the use of single nanotube sensing would obviously represent the miniaturization limit.

Nanofluidic channels and nanopores having dimensions comparable to the size of biological macromolecules such as proteins and DNA are important in applications such as single molecule detection, analysis, separation, and control of biomolecules. Previous work on nanopore or nanotube based single molecule detection can be broadly classified into two categories, namely: (i) non-functionalized nanopores; (ii) functionalized nanopores. Almost all of the prior work has involved the transmembrane protein ion channel α-Hemolysin (α HL) embedded in a suspended membrane separating two chambers filled with ionic solution. The entrance on the top (cis) side is about 2.6 nm in diameter whereas the narrow channel through the membrane that is closer to the bottom end (trans) is 1.4 nm in diameter. When a voltage bias of 120 mV is applied across the ion channel, an ionic current of about 120 pA is produced for ionic concentrations of 1 MKCI (the resistance is approximately $10^9 \Omega$). However, biological nanopores such as α-hemolysin offer single molecule sensitivity but are labile and difficult to handle.

However, inorganic channels on solid state chips have advantages over organic channels including providing better control over channel geometry, increased mechanical, electrical, thermal and chemical stability and are more amenable to integration into functional systems.

Therefore, a need exists for nanofluidic devices and nanotube structures which can be readily implemented, such as within fluidic sensing applications. The present invention fulfills those needs and others, while overcoming the drawbacks inherent in prior nanodevice and nanostructure approaches.

BRIEF SUMMARY OF THE INVENTION(S)

Nanotubes are taught being successfully integrated with microfluidic systems to create nanofluidic devices for chemical and biochemical sensing and control. In at least one implementation a nanofluidic transistor is described which provides a fluidic analog of conventional electronic transistors, in that they allow for the electronic sensing and control of select chemical and bio-chemical constituents being fluidically communicated.

One particularly well-suited application for this technology is in single DNA molecule sensing. Inorganic nanotubes are utilized according to this aspect of the invention as they provide a high aspect ratio while exhibiting translocation characteristics in which the DNA is fully stretched. Transient changes of ionic current indicate DNA translocation events. A transition from current decrease to current enhancement during translocation was observed on changing the buffer concentration, suggesting an interplay between electrostatic charge and geometric blockage effects. These inorganic nanotube fluidic devices represent a category of devices for the study of single bio-molecule translocation with the potential for integration into nanofluidic circuits.

The integration of inorganic nanotubes into metal-oxide-solution field effect transistors (MOSo/FETs) is also described herein resulting in devices which exhibit rapid field effect modulation of ionic conductance. Surface functionalization, analogous to doping in semiconductors, can switch the nanofluidic transistors from p-type, to ambipolar and n-type field effect transistors. Transient study reveals the kinetics of field effect modulation is controlled by an ion-exchange step. Nanofluidic FETs have potential implications in sub-femtoliter analytical technology and large-scale nanofluidic integration.

The invention is amenable to being embodied in a number of ways, including but not limited to the following descriptions.

A first example of the invention is a nanofluidic device, comprising: (a) at least a first and second fluid supply structure configured for supplying a fluid containing chemical or bio-chemical species; (b) a nanotube of inorganic material which fluidly couples at least a first fluid supply structure to the second fluid supply structure; (c) at least a first and second electrode, on opposing ends of the nanotube (e.g., preferably in the nanodevice structure near where it joins to each end of the nanotube), configured for establishing electrical contact with the fluid in the nanotube; and (d) means for detecting or controlling the motion of the chemical or biochemical species flowing through the nanotube. Examples of the fluid supply structure include the use of channel structures, nanopore structures, and the like.

In one mode of the invention the apparatus is configured for detecting molecular species, but not for controlling movement. In this mode the means for detecting or controlling is configured for detecting a change of current passing through the nanotube between the first and second electrode. One implementation of this means of detecting current changes comprises: (a) a voltage source configured for establishing a biasing current between the first and second electrode, the biasing current passing through the fluid which comprises an ionic solution containing molecules to be detected; and (b) a current detection circuit configured for registering transient changes in the biasing current in response to the translocation of the molecules through the nanotube.

In a second mode of the invention the apparatus is configured for controlling the movement of ionic species. In this mode the means for detecting or controlling comprises: (a) a gate electrode configured for controlling the flow of ions between at least the first and second fluid supply structure in response to the voltage applied to the gate electrode; (b) wherein the gate electrode is retained proximal the inorganic nanotube (e.g., preferably fully or partially surrounding a portion of the nanotube); and (c) wherein the nanofluidic device operates as a field-effect transistor (FET). It will be appreciated that the gate structure can be configured to operate in either detection, control, or detection and control modes.

Another example of the invention is a nanofluidic sensor, comprising: (a) a nanofluidic system configured for receiving DNA molecules, or other similarly sized molecular chains, retained within a fluid; (b) an inorganic nanotube coupled to the nanofluidic system through which the DNA molecules can be passed; and (c) means for detecting transient current changes through the fluid in response to translocation of the DNA molecules passing through the nanotube. The fluid is ionic and preferably has a known concentration. As a DNA sensor, the nanotube is configured to stretch the DNA molecule while it is passing through the nanotube, for example in response to the nanotube having a sufficiently high aspect ratio to confine the entire DNA molecule during translocation.

This nanofluidic system is preferably configured with nanopores (e.g., membrane nanopores), channels (e.g., nanochannels), or a combination of nanopores and channels for supplying a fluid containing the DNA molecules, or other large molecules, to be passed through the nanotube. In one example, at least one access hole is provided in the microfluidic system through which the fluid is communicated to the nanotube. The nanotube can be modified or functionalized to change its translocation characteristics, such as to make it more specific to selected chemical or bio-chemical molecules. In one mode of the invention, the translocation of the molecules to be detected (e.g., DNA molecules) is electrophoretically driven.

In one implementation of the nanofluidic sensor the means for detecting transient current changes comprises: (a) electrodes positioned toward opposing ends of the nanotube and configured for establishing contact with the fluid which comprises an ionic solution; (b) a voltage source configured for establishing a biasing current through the ionic solution; and (c) means for detecting transient changes in the biasing current in response to the translocation of the DNA molecules.

Another example of the invention is a nanofluidic transistor, comprising: (a) a fluidic source; (b) a fluidic drain; (c) an inorganic nanotube coupled in fluidic communication between the fluidic source and fluidic drain; (d) a gate electrode retained proximal the inorganic nanotube for controlling the flow of ions (e.g., anions, cations, or both) between source and drain regions in response to the voltage applied to the gate electrode. In this aspect of the invention, the nanofluidic transistor operates as a field-effect transistor (FET) and, more preferably, a metal-oxide-solution field effect transistor (MOSolFET).

The fluidic transistor is configured to conduct either or both ionic polarities in response to voltage applied to the gate electrode. Depending on the configuration of the nanotube, the transistor comprises a p-type, n-type or ambipolar field effect transistor. The transistor exhibits rapid field effect modulation of ionic conductance. The voltage applied to the gate electrode of the transistor shifts the electrostatic potential distribution inside the nanotubes. In at least one implementation, the nanotube comprises a silica material and is configured to have a diameter comparable with the diffuse layer of the electrical double layer (EDL) which forms in the nanotube to screen the surface potential which remains non-zero even at the center of the nanotube.

Another example of the invention is a method of detecting molecular species, comprising: (a) establishing a flow path of ionic fluid through an inorganic nanotube configured with a diameter and length adapted for translocation of single molecules of desired molecular species; (b) conducting a current through the ionic fluid in the inorganic nanotube; and (c) detecting current transients in response to a translocation event of the desired molecular species. Additionally, the movement of molecules through the tube can be controlled in response to applying a voltage to a gate disposed adjacent the nanotube between its two ends.

Another example of the invention is a method of controlling molecular flow in a fluid, comprising: (a) communicating ionic fluid through an inorganic nanotube between a first end and second end; (b) establishing a bias current between the first end and second end which passes through the ionic fluid disposed in the inorganic nanotube; and (c) controlling ionic movement through the nanotube in response to a level of voltage applied to a gate electrode which is retained between the first and second ends of the nanotube.

It is preferable that the nanotube is configured with a sufficiently small diameter so that an electrical double layer (EDL) forms whose diffuse layer extends at least to the approximate center of the nanotube, thus rendering full control of movement across the whole cross-section of the nanotube. In addition, the nanotube can be functionalized to aid in selectively controlling the movement of molecules through the nanotube. For example, functionalizing can provide for selective control of the movement of anions, cations, or both anions and cations, through the nanotube.

Described within the teachings of the present invention are a number of inventive aspects, including but not necessarily limited to the following.

An aspect of the invention is a nanofluidic device technology providing for the electrical sensing and control of chemical and bio-chemical constituents.

Another aspect of the invention is to provide a nanofluidic device which provides reproducible detection of ionic and molecular species.

Another aspect of the invention is to provide a nanofluidic device which can be fabricated in a planar layout, and which for example may allow for both optical and electrical probing.

Another aspect of the invention is to provide a nanofluidic device which can benefit from the use of self-assembly techniques.

Another aspect of the invention is to provide a nanofluidic device for sensing continuous flows or volumes down to sub-femtoliter regimes.

Another aspect of the invention is to provide a nanofluidic device for sensing fluids communicated through a fluid supply structure, such as channel structures and/or nanopores.

Another aspect of the invention is to provide a nanofluidic device which can be integrated with membrane nanopores.

Another aspect of the invention is to provide a nanofluidic device comprising chemically synthesized inorganic nanotubes within a nanofluidic system.

Another aspect of the invention is to provide a nanofluidic device incorporating inorganic nanotubes, which do not repel water, and within which a charged-oxide surface forms in response to filling with an ionic fluid under a bias potential.

Another aspect of the invention is to provide a nanofluidic device comprising nanotubes having a high aspect ratio, such as having a length on the order of 10 µm, or more preferably of approximately 10 µm.

Another aspect of the invention is to provide a nanofluidic device using high aspect ratio nanotubes configured to confine entire bio-molecules toward registering translocation characteristics.

Another aspect of the invention is to provide a nanofluidic device configured for DNA molecular sensing.

Another aspect of the invention is to provide a nanofluidic device configured to determine single molecule translocation in response to detecting current changes through the fluidic channel.

Another aspect of the invention is to provide a nanofluidic device filled with a fluid, preferably an ionic solution, through which a biasing current can be passed along the length of the passage within the nanotube.

Another aspect of the invention is to provide a nanofluidic device in which ionic current drop events are attributable to the geometrical exclusion effect of conducting ions because of the finite size of λ-DNA which leads to transient ionic current blockage.

Another aspect of the invention is to provide a nanofluidic device configured for detecting DNA whose translocation is electrophoretically driven.

Another aspect of the invention is to provide a nanofluidic device configured for utilizing the critical ion concentration $n_{cr}$.

Another aspect of the invention is to provide a nanofluidic device having at least one nanotube through which fluid conveyance is controlled.

Another aspect of the invention is to provide a nanofluidic device configured as a nanofluidic FET, and more particularly a metal-oxide-solution field effect transistor (MOSo/FET).

Another aspect of the invention is to provide a nanofluidic FET device which can be configured to selectively conduct either or both ionic polarities.

Another aspect of the invention is to provide a MOSo/FET transistor device which exhibits rapid field effect modulation of ionic conductance.

Another aspect of the invention is to provide a fluidic FET transistor wherein gate voltage changes shift the electrostatic potential distribution inside the nanotube.

Another aspect of the invention is to provide a nanofluidic device in which the kinetics of field effect modulation are controlled by an ion-exchange step.

Another aspect of the invention is to provide a nanofluidic FET device incorporating a silica nanotube through which ionic species are passed.

Another aspect of the invention is to provide a nanofluidic FET device incorporating a nanotube having an inner diameter on the order of 50 nm, or thinner, and a length on the order of 10-20 µm.

Another aspect of the invention is to provide a nanofluidic FET device incorporating a nanotube having an inner diameter of approximately 40-50 nm, or thinner, and a length of approximately 10-20 µm.

Another aspect of the invention is to provide a nanofluidic FET device having a transparent cover through which the interior of the device can be viewed.

Another aspect of the invention is to provide a nanofluidic FET device having a cover of polydimethylsiloxane (PDMS).

Another aspect of the invention is to provide a nanofluidic device subject to unipolar ionic transport under certain conditions of concentration and biasing.

Another aspect of the invention is to provide a nanofluidic FET device in which the inner surface, or portions thereof, of the nanotube is modified to control conductance.

Another aspect of the invention is to provide a nanofluidic FET device which utilizes surface functionalization in an analogous manner to which doping of semiconductors is performed, toward switching nanofluidic transistors from p-type, to ambipolar, and n-type field effect transistors.

Another aspect of the invention is to provide a nanofluidic FET device which is functionalized with three-amino-propyltrietheoxylsilane (APTES), or similar.

Another aspect of the invention is to provide a nanofluidic FET device in which an electrical double layer (EDL) forms in the nanotube to screen the surface potential.

Another aspect of the invention is to provide a nanofluidic FET device in which the diameter of the nanotube is comparable with the diffuse layer of the EDL so that electrical potential remains non-zero even at the center of the nanotube.

Another aspect of the invention is to provide a nanofluidic FET device having at least one nanotube whose inner surfaces are modified to change the surface potential, charge density and/or even switch the polarity of the channel.

Another aspect of the invention is to provide a nanofluidic FET device in which the inner surfaces of the nanotube are modified by being functionalized, such as treated with three-amino-propyltrietheoxylsilane (APTES), or similar, according to a treatment regime and period.

Another aspect of the invention is to provide a method of detecting the movement of chemical and bio-chemical species through a nanotube.

Another aspect of the invention is to provide a method of controlling the movement of chemical and bio-chemical species through a nanotube.

Another aspect of the invention is to provide a method of both detecting and controlling the movement of chemical and bio-chemical species through a nanotube.

A still further aspect of the invention is to provide mechanisms for precisely detecting and controlling fluidic flow on a nanoscale level.

The present invention also pertains to fluidic nanotubes and devices fabricated from functionalized fluidic nanotubes. The fabrication of oriented, robust nanotube arrays is of use in nanoscale fluidic bioseparation, sensing, catalysis, and the like. The apparatus and methods of the present invention can be adapted to many different detection, separation and analytical applications and nanofluidic contexts. Although specific examples are used as illustrations, it will be understood that the apparatus and methods will be useful for any scheme that would benefit from intentional manipulation of ionic or electrostatic conditions within a nanochannel or nanochannel geometry.

Electronic detection of biomolecules with nanofluidic channels and nanopores having dimensions comparable to the size of biological macromolecules can serve as a highly selective and sensitive sensor that is compatible with current "lab-on-a-chip" micro-total-analysis systems. Miniaturized sensors or bioassays have three fundamental components: 1) a transport system for loading a sample and flushing fluid; 2) a sensing unit that produces a measurable signal or indicator in the presence of the molecule, and 3) a functionalized element that is part of the sensing unit configured to interact with an analyte.

The fluid transport system is generally connected to at least one nanotube with a nano-scale central channel. Flow through the nanochannel may be passive or may be active with the assistance of electroosmotic forces with the use of electrodes and may also include a means for controlling the flow of fluid and ions through the channels, such as a set of gate electrodes.

The sensing unit includes a means for determining conduction along the nanotube. Optionally, the sensing unit may also have an optical sensor used in combination to provide potential detection of labeled analytes.

The sensor preferably comprises a nanotube with a central channel that is functionalized with a plurality of biomolecules. The biomolecule may be a receptor or ligand, globular protein or some other molecule that will interact with an analyte of interest. The biomolecule may also serve to change the geometry, analyte flow rate or regulate ionic conditions within the nanochannel.

Another class of devices fabricated from fluidic nanotubes includes a nanofluidic transistor formed from a semiconductor nanotube and having source and drain connections, and optional gate electrode along the length of the nanotube. By way of example, another class of devices fabricated from fluidic nanotubes, which have been functionalized, comprises electrophoretic devices formed from insulating or semiconducting nanotubes, and having source and drain electrodes within the reservoirs proximal to each open end of the nanotubes. From these classes of fluidic devices, separately or in combination, numerous fluidic devices can be implemented, which include but are not limited to, nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, transistors, sensors, thermoelectric devices, photonic devices, nanoelectromechanical actuators, nanoelectromechanical sensors, and imaging devices. It will be appreciated that the devices described herein are based on the use of fluidic nanotubes in general; that is, their fabrication need not be based on a specific composition of nanotube but on the use of a fluidic nanotube.

The ability to spacially and temporally tune the ionic and electrostatic environment within a nanotube channel will allow the manipulation of small quantities of charged biomolecules for biological analyses on solid state chips. The capability of ionic environmental control can be integrated into existing microfluidic and nanofluidic circuits and schemes.

According to one aspect of the invention, a nano-scale detector is provided with a non-organic nanotube with a channel functionalized with a biomolecule and a means for detecting conductance of the nanotube.

According to another aspect of the invention, a functionalized fluidic nanotube is provided with a tubular member having first and second ends, and an inner bore between said first and second ends having a diameter of approximately 100 nanometers or less with a non-porous inner wall. A layer of biomolecules forming a lining on the inner wall of the tubular member; and means for measuring conductance of the tubular member.

Another aspect of the invention also provides a means for varying the concentration of ions in a fluid presented to the inner bore of the tubular member and a means for creating an electric field within the tubular member.

A further aspect of the invention is to provide a functional component of a device selected from the group of devices consisting essentially of nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, transistors, sensors, thermoelectric devices, photonic devices, nanoelectromechanical actuators, nanoelectromechanical sensors, nanoscale fluidic bioseparators, and imaging devices.

According to another aspect of the invention a method of controlling the geometry of a nanofluidic channel is provided comprising immobilizing biomolecules in a nanofluidic channel and exposing said biomolecules to a solution with a high concentration of ions.

A method of detecting the presence of a binding events between biomolecules is also provided, comprising the steps of immobilizing a plurality of first biomolecules on nanochannel surface and measuring nanochannel conductance, exposing said immobilized biomolecules to an ionic solution containing a second biomolecule and measuring the conductance of said nanochannel a second time and then comparing said first conductance measurement and said second conductance measurement to determine a change in conductance. The conductance measurements can also be taken in the presence of low and high ion concentration solutions and compared.

An aspect of the invention is a method of controlling conductance characteristics of a nanofluidic channel (nanochannel), comprising immobilizing biomolecules in said channel. In one embodiment, the biomolecules comprise streptavidin. In one mode, the biomolecules modify surface charge. In another mode, the biomolecules occlude a portion of said nanochannel. In a further mode, the biomolecules alter nanochannel geometry. In another mode, immobilization of streptavidin in the nanochannel modifies surface charge and nanochannel geometry.

Another aspect of the invention is a method of controlling surface charge and device geometry in a nanofluidic channel (nanochannel) comprising immobilizing streptavidin in the nanochannel.

Another aspect of the invention is a method of sensing surface charge in a nanochannel, comprising measuring nanochannel conductance.

Another aspect of the invention is a method of detecting presence of biomolecules immobilized on nanochannel surfaces, comprising measuring nanochannel conductance.

Another aspect of the invention is a method of sensing surface charge and the presence of biomolecules immobilized on nanochannel surfaces in both surface charge-governed and geometry-governed regimes, comprising measuring nanochannel conductance.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 is a schematic of an inorganic nanotube nanofluidic device according to an embodiment of the present invention, showing a single nanotube bridging two microfluidic channels to form the nanofluidic system.

FIG. 2 is an image rendition of a fully packaged nanotube device according to an embodiment of the present invention.

FIG. 3 is a rendition of a SEM image for a nanofluidic device according to an aspect of the present invention, shown prior to attachment of the cover.

FIGS. 21A-21B are graphs of measured "APTES 4 day" ionic conductances (S) and the effective conductance at gate controlled regions ($S_{GC}$) according to an aspect of the present invention.

FIG. 22 is a graph of field effect modulation of ζ potentials for as-made and all functionalized devices according to an aspect of the present invention, with inset showing the three-capacitor model.

FIG. 23 is a graph of surface charge densities for as-made and all functionalized devices according to an embodiment/aspect of the present invention.

DETAILED DESCRIPTION OF THE INVENTION

Figure 4:
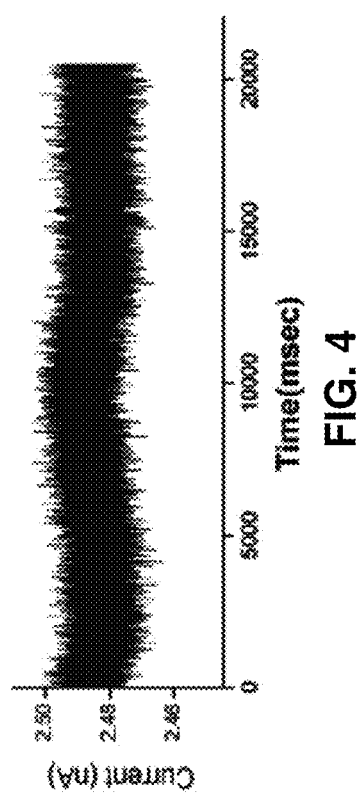
FIG. 4 is a graph of ionic signals during λ-DNA translocations with 2M KCl buffer fluid in both microchannels according to an aspect of the present invention.

The present invention will now be described with reference to FIG. 1 through FIG. 39. It will be appreciated that the apparatus may vary as to configuration and as to details of the parts, and that the method may vary as to the specific steps and sequence, without departing from the basic concepts as disclosed herein.

Inorganic Nanotubes And Devices Fabricated Therefrom

1. DNA Translocation in Inorganic Nanotubes.

The detection of individual bio-molecules has been realized in nanofluidic devices according to the present invention for which potential applications exist ranging from single molecule study of biological activity to rapid diagnosis of diseases. Biological nanochannels/pores, e.g., $\alpha$-hemolysin, have been used for detecting single-stranded polynucleotides, and show substantial promise for ultrafast DNA sequencing. Recently, artificial inorganic nanopores are attracting increasing attention due to the robustness of solid-state nanopore membranes, the flexibility of surface modification, and the precise control of nanopore sizes. The artificial nanopores have been used to study analytes ranging from small molecules, single-stranded polynucleotides to double-stranded DNAs (dsDNAs). The molecular translocation can be probed from ionic current signals. In addition, nanotubule membranes have been used to sense DNAs with single base mismatch selectivity.

Inorganic nanotubes, which represent a new class of one-dimensional nanostructures (e.g., elongate high-aspect ratio structures), are attracting increasing attention. Inspired by nanopore technology, chemically synthesized inorganic nanotubes are utilized as the core elements and integrated with nanofluidic systems for single-molecule sensing. Compared with traditional nanopore devices, these nanotube devices feature three distinct differences. First, these nanotubes have a length on the order of approximately 10 μm, thus providing a very high aspect ratio, which for example can confine the entire bio-molecule, which is likely to result in new translocation characteristics. Second, the nanotube devices taught herein provide a planar layout, which could enable simultaneous optical and electrical probing. Third, the current device geometry of these nanotube devices is compatible and amenable to integration with lab-on-a-chip micro-total-analysis systems (μTAS), and microelectronics. Moreover, advancing self-assembly techniques, such as Langmuir-Blodgett assembly, provide convenient routes for fabricating large-scale arrays of nanofluidic devices for parallel processing.

1.1 Example

Nanofluidic Device 1

FIG. 1 illustrates an example embodiment 10 of a nanotube nanofluidic device that features a single inorganic nanotube 12 bridging two microfluidic fluid supply structures, depicted here as channels 14, 16, mounted to a base 20, such as a silica substrate. The channels are shown with access holes 18a, 18b, 18c and 18d. It should be appreciated that although the fluid supply structure is shown comprising a channel structure (e.g., nanochannel), it can also be configured with a nanopore structure (e.g., nanoporous membrane) or combination thereof.

Uniform silicon nanowires were utilized during testing which had a controlled wall thickness and a pore size down to about 10 nm. By way of example, nanowires for use in the nanofluidic device can be chemically synthesized, such as by $SiCl_4$ chemical vapor deposition, and translated into silica nanotubes through an oxidation/etching process. Nanotubes utilized in testing had an inner diameter of typically 50 nm or less.

FIG. 2 is a representation (rendition) of an actual SEM image taken of a fully packaged nanofluidic device with microfluidic channels and inlet/outlet ports.

FIG. 3 is another representation (rendition) of an actual SEM image showing the integration of a single nanotube with microfluidic channels. Scale bar 10 μm. The cross-sectional view (inset) clearly shows the opening of the nanotube embedded between two silicon dioxide layers. It should be appreciated that the open end of the nanotube section will be fluidically available on either side of the wall separating the nanofluidic channels.

Figure 5:
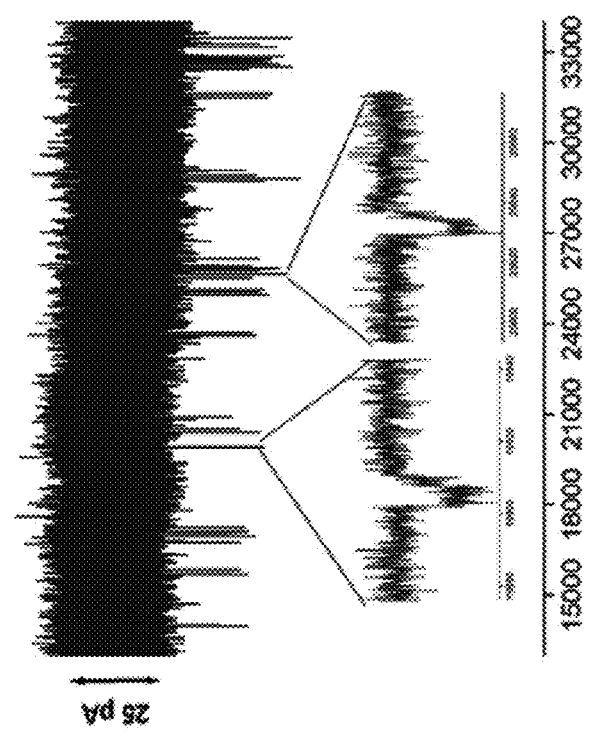
FIG. 5 is a graph of a typical ionic current signal according to an aspect of the present invention, shown with magnification of the current axis.
Figure 6:
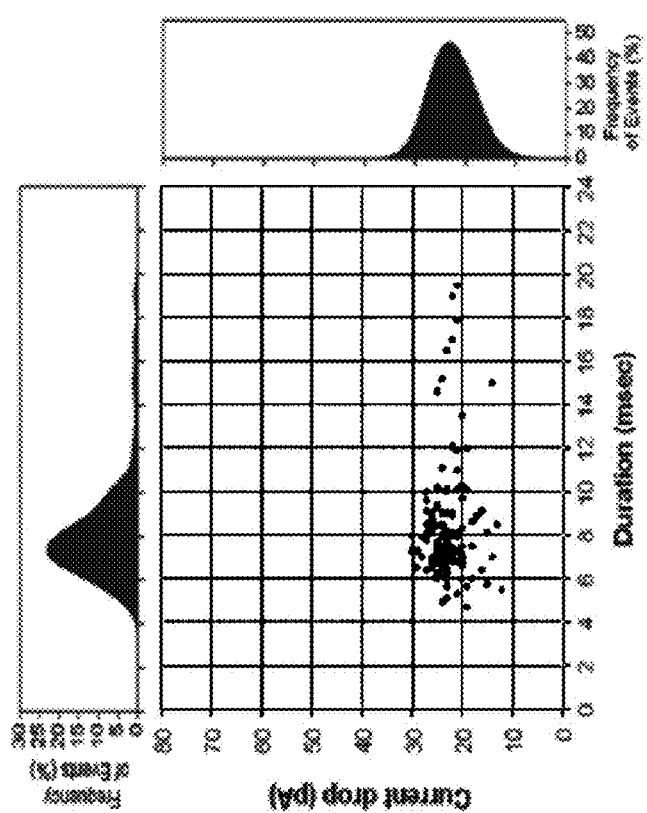
FIG. 6 is a graph of current drop and duration time for three measurements according to an aspect of the present invention.

FIG. 4 through FIG. 6 illustrate electrical characteristics of the nanofluidic device of FIG. 2 during testing of $\lambda$-DNA translocations in an aqueous solution of a first concentration of buffer solution in both microchannels. In these tests both microfluidic channels were filled with 2M potassium chloride (KCl) buffer solution, and ionic current was recorded in FIG. 4 in response to applied voltage bias. All fluid solutions in these tests were prepared with DNA buffer solution, which consists of 10 mM NaCl, 10 mM Tris-HCl and 1 mM EDTA in aqueous solution with pH=7.6. No transient current change was observed although the baseline shifted slightly over time. When $\lambda$-DNA molecules in 2 M KCl buffer were introduced to the negatively biased microchannel while the other microchannel was filled only with buffer solution, the ionic current exhibited frequent drops in current as seen in FIG. 5, which corresponded with the passage of $\lambda$-DNAs through the nanotube. The graph shows typical ionic current signals recorded when a $\lambda$-DNA (~30 μg/mL) test solution (prepared with 2M KCl buffer) was loaded to the negatively biased (0.4V) microchannel, in response to which extensive current drop spikes were seen. Current drop signals were not observed when the bias polarity was reversed.

These current drop events may be attributed to the geometrical exclusion effect of conducting ions because of the finite size of $\lambda$-DNA, leading to transient ionic current blockage. Although, the noise level is relatively high, these ionic current drops can still be resolved and were highly reproducible. Statistics of current drop and duration for three measurements are shown in FIG. 6. The main plot shows the pattern of all events, with a tight distribution indicating a single molecule translocation scheme. The top and right insets are the event frequency as a function of duration time and current drop, respectively. The typical current change was 10 to 40 pA; the typical duration was 4-10 mS with a small fraction of events up to 20 mS. The overall distribution was quite narrow and centered around 23 pA and 7.5 mS, suggesting that most of the events were identical, corresponding to single molecule translocation.

Furthermore, once the polarity of the applied bias was reversed no signal peaks were observed, indicative of the DNA translocation being electrophoretically driven. For electrically charged particles (spherical particles) in aqueous solution, the electrophoretic mobility is roughly approximated by $\mu_{EP}=q/6\pi\eta r$ (wherein q is the charge of particles, $\eta$ is the viscosity, and r is the particle size).

Since the persistence length of double-stranded DNA is about 50 nm it is likely that the DNA molecules are fully stretched in the nanotube with a diameter of 50 nm. The particle size r can be approximated by the end-to-end distance of the stretched DNA molecule. The end-to-end distance $L_z$, estimated using de Gennes dynamics model, is about 5.8 µm. It is of interest that an experimental study of stretching λ-DNA in nanochannels gave an average $L_z$ about 8 µm. This means that the entire λ-DNA molecule could stay inside the nanotube during translocation. The electrophoretic mobility of λ-DNA in the nanotube is calculated to be approximately 1×10-8 m2/Vsec and the resulting DNA transport velocity is about 2 µm/mS under a bias potential of 1 volt.

Consequently, the predicted translocation duration is 2.5 mS, which is in agreement with the shortest limit of observed events. Due to the interactions of biomolecules with the surface electric double layer, it is reasonable to expect a longer translocation time. Moreover, electro-osmotic flow could add an opposite force to slow down the translocation of DNA molecules.

1.2 Example

Nanofluidic Device 2

Figure 9:
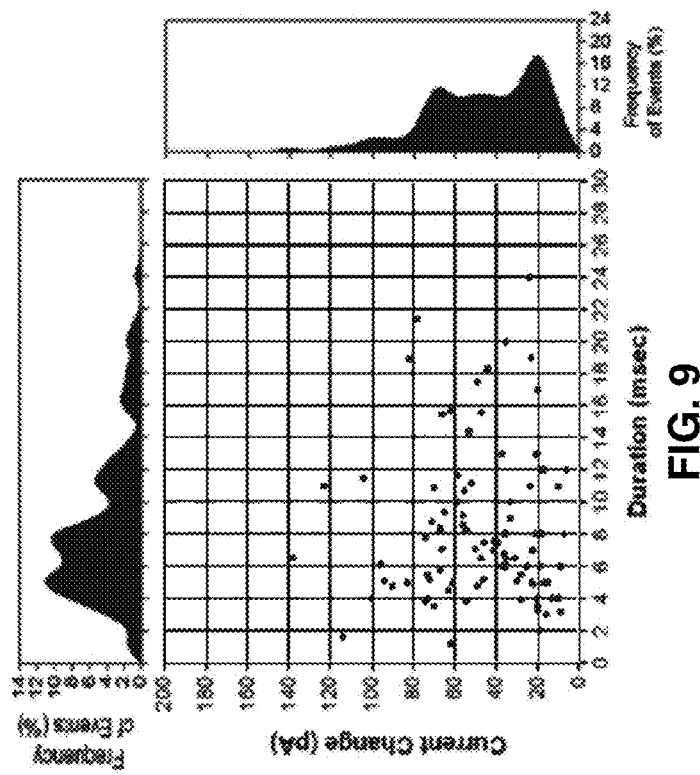
FIG. 9 is a graph of current drop and duration time for four measurements according to an aspect of the present invention.
Figure 7:
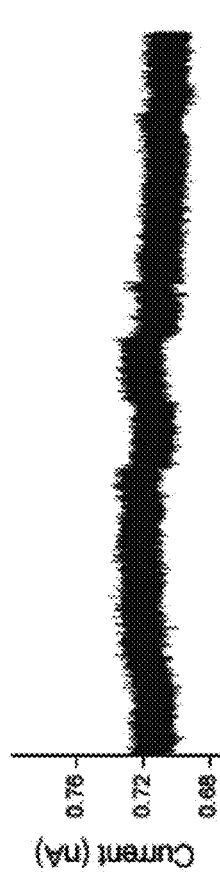
FIG. 7 is a graph of ionic current signals in response to λ-DNA translocations with 0.5M KCl buffer according to an aspect of the present invention.
Figure 8:
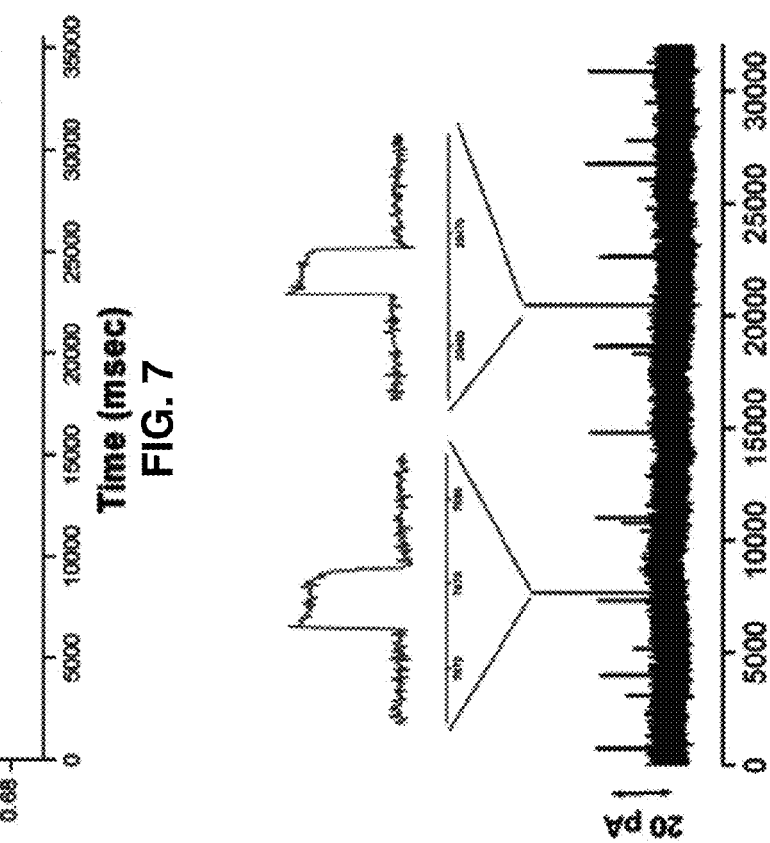
FIG. 8 is a graph of typical ionic current signal recorded when λ-DNAs (~6 μg/mL) test solution of 0.5M KCl buffer was loaded to microchannel according to an aspect of the present invention, shown with magnification of the current axis.

FIG. 7 through FIG. 9 illustrate electrical characteristics of the nanofluidic device during the same testing, as shown in FIG. 4 through FIG. 6, in a second aqueous solution having a second, lower, concentration of KCl (0.5 M) buffer solution, wherein a distinctly different phenomenon was observed. In FIG. 8 a typical ionic current signal is shown when λ-DNAs (~6 µg/mL) test solution (prepared with 0.5M KCl buffer) was loaded to the negatively biased (1V) microchannel. Instead of a current decrease in response to translocation, as seen in FIG. 4 through FIG. 6, frequent current increases were observed corresponding to the passage of λ-DNA molecules. The control experiment exhibited some baseline shifts as seen in FIG. 7, although no abrupt current changes were observed. FIG. 9 depicts current drop and duration time for four measurements; the main plot shows the pattern of all events showing a relatively broader distribution. The top and right insets depict the event frequency as a function of duration time and current drop, respectively.

It should be appreciated that translocation characteristics were different compared with the 2M KCl case, wherein the statistics of current change and duration time showed a much broader distribution. This appears to be the first observation of ionic current crossover, for example a transition from current blockage to current enhancement during DNA translocation through nanotubes as a result of their unique dimensions. Ionic current increase during DNA translocation through 50 nm to 60 nm long nanotubes was previously observed by Chang et al. The current enhancement was attributed to the introduction of counterions in the nanotube due to the charge on DNA molecules dominating over the steric blockage effect observed in other studies. Tests on the nanofluidic devices confirm their observations and further elucidate that there is a crossover from current enhancement to current blockage that depends on ionic concentration.

When DNA molecules enter the nanotube, the number of cations and anions in the nanotubes would decrease due to the volume exclusion effect. At the same time, DNA molecules also carry counterions (cations) into the nanotube, which may transiently increase the cation concentration. A simple model is developed here which build on the arguments presented by Chang et al., in the article: Chang, H.; Kosari, F.; Andreadakis, G.; Alam, M. A.; Vasmatzis, G.; Bashir, R. *Nano. Lett.* 2004, 4, 1551. Assuming that Manning condensation (refer to Manning, G. *Biophys. Chem.* 2002, 101, 461.) of counter-ions neutralizes a fraction (1-φ) of the negative phosphate groups of DNA leaving fraction φ for mobile counter-ions to interact with, the change Δn in the mobile counter-ion density inside the nanotube is:

$$\Delta n = \Delta n_{CHARGE} + \Delta n_{BLOCK} = \frac{2\phi b}{N_A V_{nt}} - \frac{V_{mol}(n_+ + n_-)}{V_{nt}} \quad (1)$$

where b is the number of base pairs (48500 for λ-DNA), $V_{nt}$ is the volume of the nanotube, $V_{mol}$ is the volume occupied by the DNA molecule, $n_+$ and $n_-$ are the cation and anion densities, respectively, within the nanotube in the absence of DNA, and $N_A$ is Avagadro's number. The first term ($\Delta n_{CHARGE}$) corresponds to the increase in mobile counter-ion concentration due to the presence of DNA (e.g., the molecular gating effect), whereas the second term ($\Delta n_{BLOCK}$) is the steric exclusion of both cations and anions. It should be recognized that the expression for $\Delta n_{CHARGE}$ is only approximately given by Eq. (1). In these tests KCl was used as the electrolyte, although it will be appreciated that various other electrolytes may be utilized according to application and characteristics without departing from the teachings of the invention. The ionic mobilities for $K^+$ and $Cl^-$ are $\mu_{K+}$ at approximately 7.62×10$^{-8}$ m$^2$/Vs and $\mu_{Cl-}$ at approximately 7.91×10$^{-8}$ m$^2$/Vs, respectively. So the current change during DNA molecule translocation is given by:

$$\Delta I = \Delta I_{CHARGE} - \Delta I_{BLOCK} \quad (2)$$
$$= \left\{ \Delta n_{CHARGE} \cdot \mu_{K'} - \left(\frac{\Delta n_{BLOCK}}{2}\right)[\mu_{K'} + \mu_{Cl}] \right\} e \cdot N_A \cdot A \cdot E$$

where A is the cross sectional area of the nanotube, E is the magnitude of the electric field across the nanotube. The values $\Delta n_{CHARGE}$ and $\Delta n_{BLOCK}$ denote the current changes corresponding to the charge effect and the steric blockade effect, respectively. Current carried by a translocating biomolecule itself is negligible compared to ionic current due to low biomolecular mobility.

Figure 11:
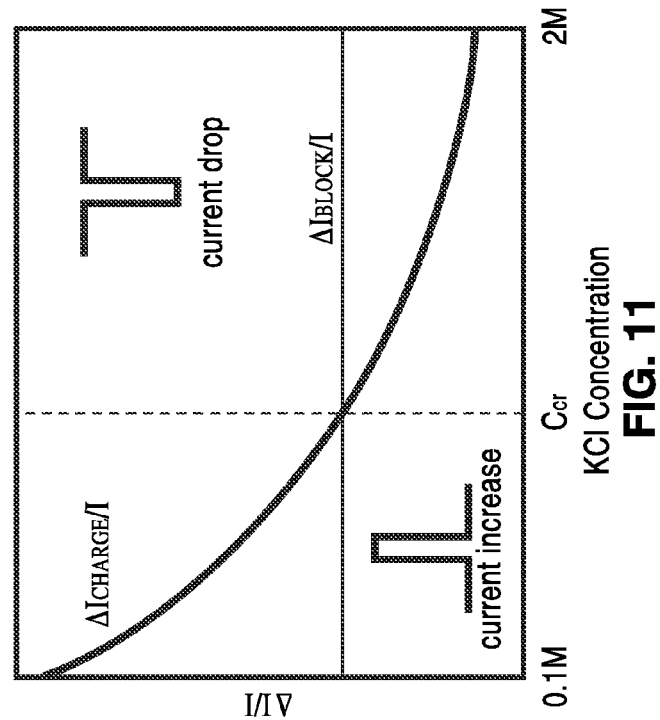
FIG. 11 is a graph of the interplay between charge effect and blockade effect according to an aspect of the present invention.
Figure 10:
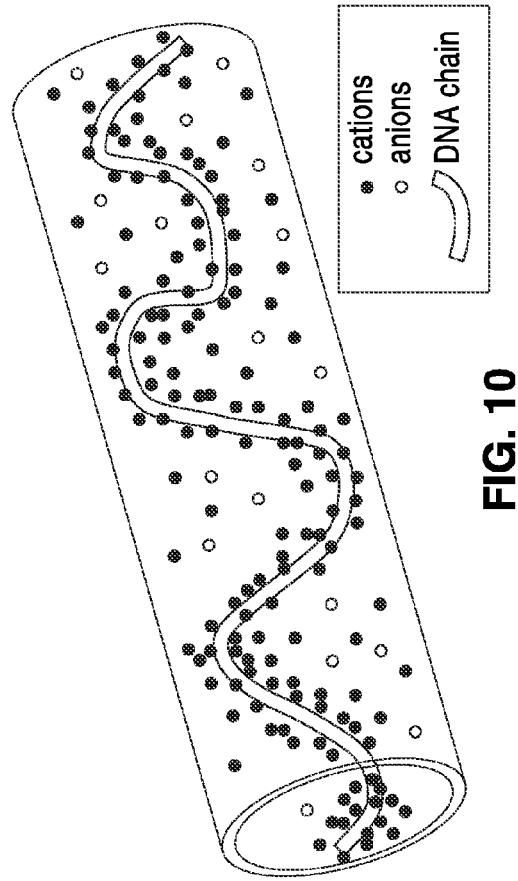
FIG. 10 is a schematic of ionic distribution of counterions and co-ions in an inorganic nanotube when a DNA molecule is confined therein according to an aspect of the present invention.

FIG. 10 and FIG. 11 illustrate ion distribution for the nanotube in the nanofluidic device. FIG. 10 depicts ionic distribution of counterions and co-ions in an inorganic nanotube when DNA molecules are confined inside. FIG. 11 depicts the interplay of charge effect and blockade effect of Eqs. (1-2) which shows that a critical ion concentration $n_{cr}$ exists such that $\Delta I > 0$ when $\Delta I_{CHARGE} > \Delta I_{BLOCK}$, and $\Delta I < 0$ when $\Delta I_{CHARGE} < \Delta I_{BLOCK}$. The critical total ion concentration is given as:

$$n_{cr} = \frac{4\phi b}{V_{mol} N_A} \left( \frac{\mu_K}{\mu_{K+} + \mu_{Cl-}} \right) \quad (3)$$

with the critical KCl concentration at $c_{cr}=n_{cr}/2$. Note that for a linear molecule such as DNA, $V_{mol}=\pi r^2 p b$, where r is the radius of the double helix and p is the length per base pair (e.g., 0.34 nm). For dsDNA molecules, φ ranges from 0.17-0.5 based on previous reports and simulation.

Here it is assumed that φ=0.5 for Manning condensation, and r=1 nm. Therefore, the critical KCl concentration is estimated as $n_{cr}$, which is approximately 0.79M.

This simple scheme indicates there is an ionic current crossover (from current blockade to current enhancement) for DNA translocation through a nanotube as the KCl concentration is decreased below the critical concentration (~0.79 M). This unexpected result has indeed been observed in our experiments. Eq. (4) predicts a net current blockade of 20 pA for 2M KCl, which again agrees very well with the experimental data (~20-30 pA). The predicted current increase for 0.5M KCl is 6 pA, which corresponds to the lowest limit in our observation. While this scheme qualitatively explains the experimental observations, it should be pointed out that this may be an over-simplified account of a highly complex DNA transport process within nanotubes filled with electrolytes.

The inorganic nanotube nanofluidic device of the present invention significantly extends the time scale of single molecule transport events compared to the use of nanopore devices. In addition, useful information on bio-molecules within a confined geometry can be obtained from duration, current change, and current decay characteristics measured at different ionic concentrations and bias currents. Therefore, the nanotube devices of the present invention represent a new platform for studying single molecule behavior. Due to their planar design and compatibility with standard microfabrication technology, this basic module of inorganic nanotube nanofluidics could enable simultaneous electrical and optical probing. Moreover, nanotube devices could be further integrated into nanofluidic circuits for high throughput and parallel analysis of biological species at the single molecule level.

1.3 Method of Detecting Molecular Species

It can be seen from the above that a number of steps are involved toward providing an ability to detect molecular species, such as DNA, from within an ionic fluid. In general, the steps of molecular detection comprise the following. A flow path is established for the ionic fluid through a nanotube. The diameter of the nanotube is adapted with a diameter and length for translocation of single molecules of the desired molecular species. Electrodes are positioned proximal each end of the nanotube to establish electrical connection with the fluid within the nanotube. A current is conducted between the electrodes and thus through the ionic fluid in the nanotube. Current transients are detected in the bias current, which indicate the occurrence of translocation events of the desired molecular species. It will be appreciated that other methods and variations can be implemented by one of ordinary skill in the art without departing from the teachings of the present invention.

2. Polarity Switching and Transient Responses.

The ability to manipulate charge carriers (electrons and holes) in metal-oxide-semiconductor field effect transistors (MOSFETs) has revolutionized how information is processed and stored, and created the modern digital age. Analogous to MOSFETs, introducing field effect modulation in micro/nanofluidic systems in a three-terminal device enables the manipulation of ionic and molecular species at a similar level and even logic operations. Inorganic nanotubes are preferably utilized in these nanofluidic transistors, such as silicon, because a charged oxide surface forms within the nanotube which facilitates attracting ions in solution. In contrast to inorganic nanotube use would be trying to utilize organic nanotubes, such as carbon nanotubes. However, organic nanotubes repel water and thus do not form the charge layers which are relied upon in these fluidic transistors. It should also be noted that due to strong Debye screening in aqueous solution, field effect modulation of ion transport arises only in systems whose dimensions are comparable to the critical Debye Length, such as in nanofluidic channels.

A nanofluidic transistor is fabricated which incorporates an inorganic nanotube configured to conduct either positively or negatively charged ions dissolved in a fluid. Charge flows through the tube in response to ions which flow through the fluidic channel nanotube as controlled by the voltage applied to the gate electrode. Modification of the nanotube, such as the degree of chemical modification or functionalization, determines whether one or both ion polarities are conducted through the nanotube depending on applied gate voltage.

Numerous applications for the technology can be considered, such as highly sensitive biological sensors, selective pumps, fluid-based "computer chips", and so forth. Manipulating individual charged molecule flow can be highly beneficial toward creating these and many other advanced chemical and biochemical systems. These fluidic transistors are capable of operating with very small quantities of material, such as femtoliter amounts of blood or saliva.

Previously, mechanical means were required in transporting small quantities of conductive fluids, such as blood, saliva or urine. However, the present invention makes use of the conductivity of these fluids toward inducing movement of the fluids. Nanofluidics has already attracted attention for ultra-sensitive or even single molecule level detection and biological activity study. For instance, membrane channel proteins and artificial solid state nanopores were utilized for single molecule sensors, configuration study, and DNA sequencing. These nanopore devices usually passively transport ionic species, similar to an electrical resistor. Analogous to unipolar MOSFETs, introducing an external electrical field to modulate ionic conductivity according to the present invention would elevate nanofluidics to a higher level of controllability or even logic. It is also notable that a single conical nanopore has been reported to exhibit active rectified ion transport in a two-terminal device configuration. Single nanochannel studies have shown that the surface charge governs the ionic transport and induces the formation of unipolar solutions as in unipolar MOSFETs. Metal nanotubule membranes exhibited selective ion flux upon electrochemically tuning surface charges. These results are indicative of feasibility toward fabricating single nanotube ionic field effect transistors. In the following tests a rapid field effect control of electrical conductance in single nanotube nanofluidic transistors was provided. Furthermore, the polarity switching of the devices could be controlled in response to the level of surface functionalization and the transient responses upon field effect control.

2.1 Example

Nanotube Ionic FET 1

Figure 12:
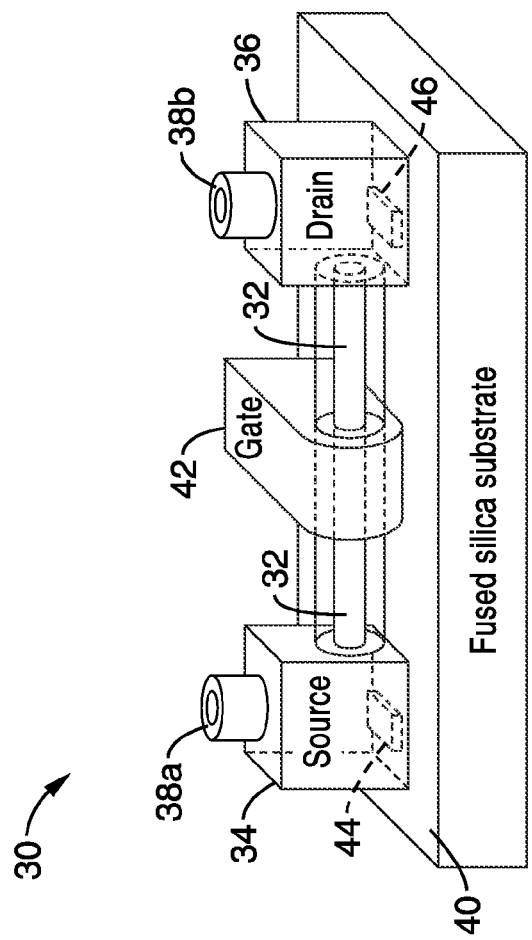
FIG. 12 is a perspective view of a single nanotube nanofluidic transistor (MOSo/FET) according to an embodiment of the present invention.

FIG. 12 illustrates an example embodiment 30 of a nanotube ionic field effect transistor. A nanotube 32 is shown coupled between a source 34 and drain 36 which are configured for passing a fluid therebetween. By way of example, the source and drain each have at least one fluid coupling means, such as access holes 38a, 38b. Source 34 and drain 36 are mounted to a base, such as substrate 40. A gate 42 is retained proximal to (e.g., preferably fully or partially surrounding) nanotube 32, with conductors 44, 46 in contact with opposing sides of the nanotube for making electrical contact with the fluid being communicated within the nanotube. For the example shown, conductors 44, 46 are contained within source 34 and drain 36 configured for establishing electrical contact with the fluid contained within nanotube 32.

Figure 13:
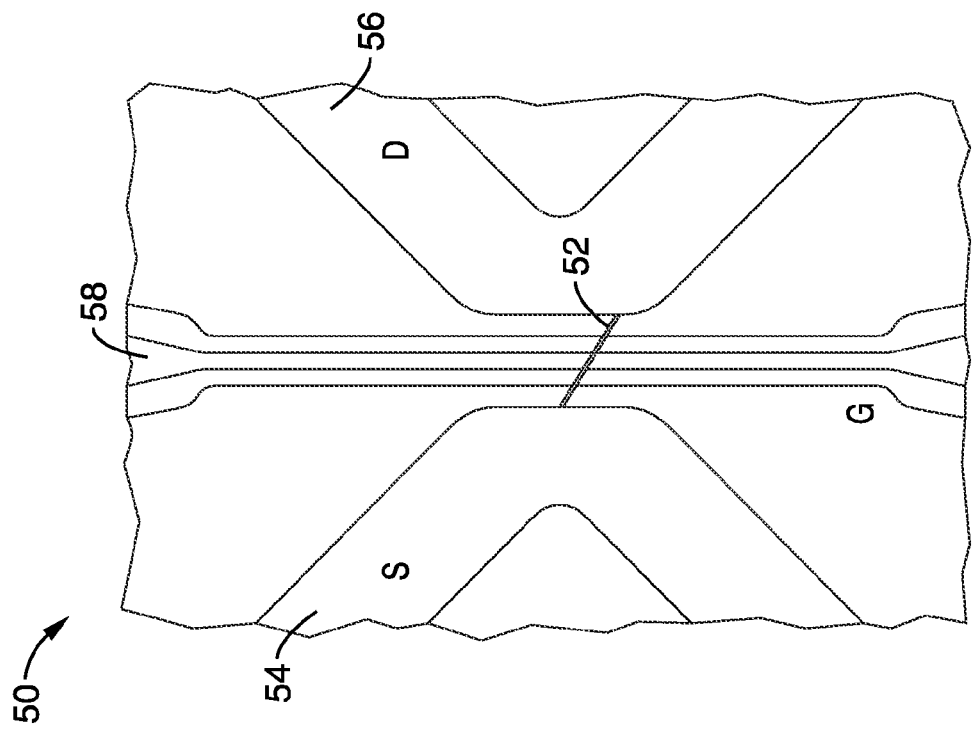
FIG. 13 is a SEM image rendition of the device structure of FIG. 13.

FIG. 13 illustrates an example implementation 50 (shown as a rendition of an actual SEM image) having nanotube 52, source channel 54, drain channel 56, and gate 58. It this embodiment the nanotube is a chemically synthesized silica nanotube with high aspect ratio, and having both excellent uniformity and surface smoothness. The nanotubes for use in this embodiment should have an inner diameter of about 40-50 nm and a length of about 15 μm. The nanotube is integrated into this single nanotube nanofluidic transistor by interfacing with the two microfluidic channels. The device includes a lithographically defined gate electrode 58, and deep etched source/drain microfluidic channels 54, 56, and a polydimethylsiloxane (PDMS) cover (not visible).

Concentration dependence of ionic conductance deviates from bulk behavior when [KCl]<10 mM, which indeed confirms the formation of unipolar ion transport, and lays down the foundation for further field effect modulation. When applying gate voltages (Vg), the electrical conductance of KCl solution ($\leq$1 mM) decreases with changing Vg from negative to positive, a characteristic of p-type transistors.

Figure 14:
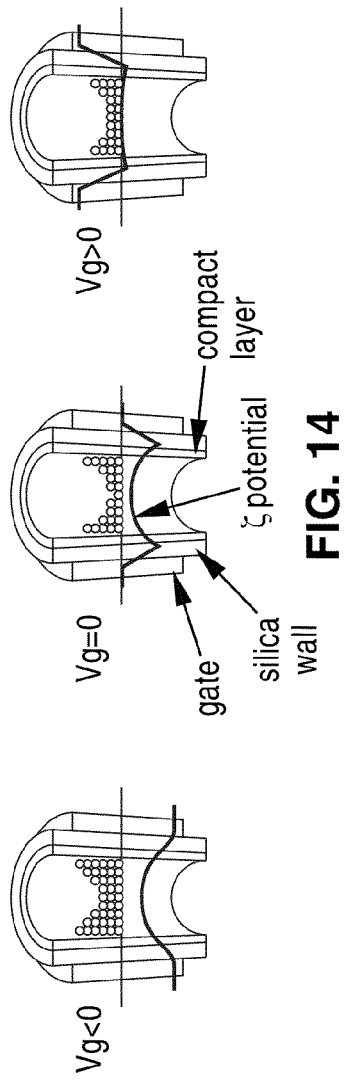
FIG. 14 is a schematic of field effect modulation of electrical potential diagram in MOSo/FETs according to an aspect of the present invention.
Figure 15:
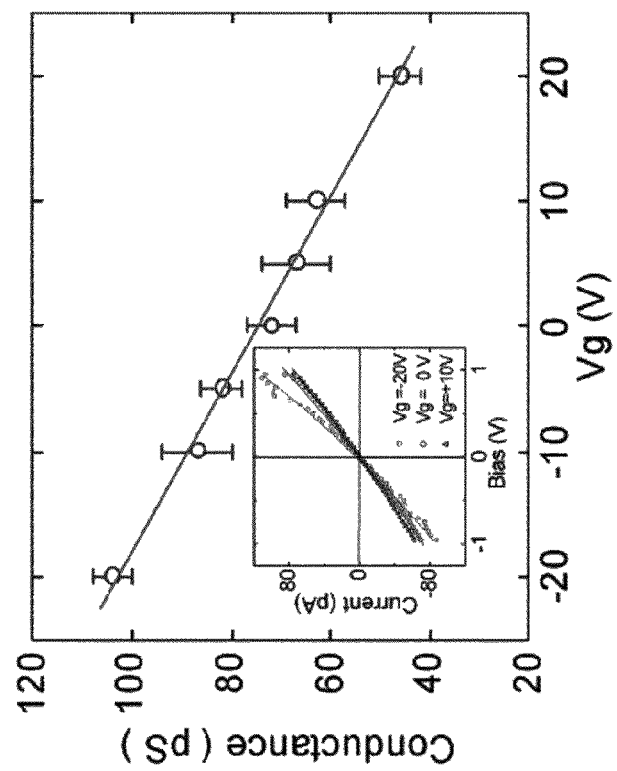
FIG. 15 is a graph of ionic conductance with respect to gate voltage for the device of FIG. 12, with an inset showing selected IN curves.

FIG. 14 and FIG. 15 illustrate shifting of electrostatic potential within the nanotube transistor. Similar to field modulation in a metal-oxide-semiconductor (MOS) system, gate voltages in the nanofluidic transistor shift the electrostatic potential distribution inside the nanotube. FIG. 14 illustrates three cases of gate voltage, specifically negative, zero and positive. In the solution an electrical double layer (EDL) forms on the interior of the nanotube to screen the surface potential. The EDL consists of an inner compact layer (Stern layer) and an outer diffuse layer. In a fluid medium sufficiently larger than the thickness of the diffuse layer, the electrostatic potential decays from the effective surface potential ($\zeta$ potential) to zero. When the solution is confined in nanotubes, whose dimension is comparable to or smaller than the diffuse layer, the electrical potential remains non-zero even in the middle of nanotubes. In the case of a silica nanotube having negative surface charges, cations are majority carriers and the resulting transistors are p-FETs. Negative Vg enhances cation concentration while positive Vg depletes cations. This simple scheme explains qualitatively how field effect control works in nanofluidic systems.

A number of benefits can be derived by tuning the "doping level", in a similar manner as doping levels are tuned in a semiconductor, to change inherent carrier concentrations or type and systematically study field effect operation in nanofluidic transistors. It is clear that inherent carrier concentrations in nanofluidic transistors are controlled by inner surface potential and charge density. In this regard, surface modification is expected to have a similar consequence for nanofluidic transistors as semiconductor doping has for MOSFETs. Reduced doping level in semiconductors is generally associated with pronounced field effect modulation. The following describes the impact of surface modification on the field effect for our metal-oxide-solution field effect transistors (MOSo/FETs) according to the present invention.

2.2 Example

Nanotube Ionic FET 2

Figure 16:
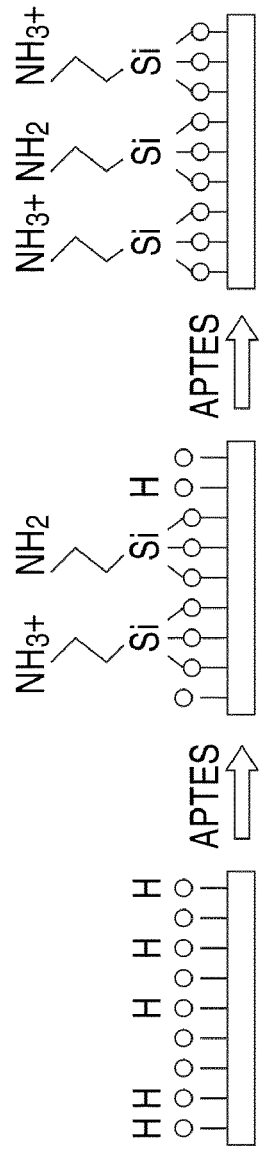
FIG. 16 is a schematic of "doping" a nanotube inner surface with APTES according to an aspect of the present invention.

FIG. 16 illustrates surface modification within the nanotube of a nanofluidic transistor. By way of example and not limitation, aminosilane chemistry was used to modify inner surfaces of silica nanotubes in order to change the surface potential and charge density or even switch channel polarity. As represented by the figure, right before PDMS cover bonding, the nanotube was treated with three-amino-propyltriethoxylsilane (APTES) while the transistor characteristics were monitored over the surface functionalization duration.

Figure 17:
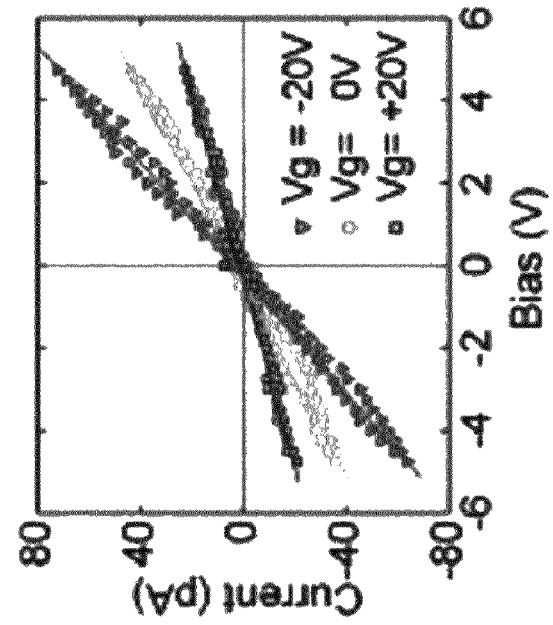
FIG. 17 is a graph of selected current/voltage (IN) curves for the nanofluidic transistor after 1 day of APTES treatment according to an aspect of the present invention.

FIG. 17 is a graph indicating that one day of APTES functionalization did not change polarity (still p-type behavior) of the material, but led to greatly reduced ionic conductance and more pronounced gating effect.

Figure 18A:
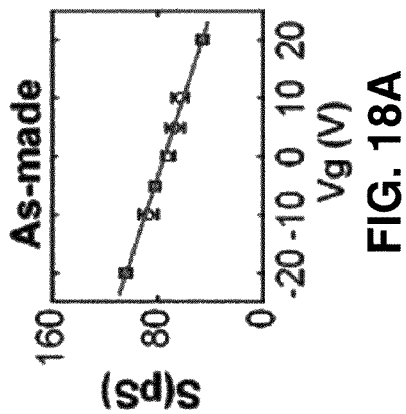
FIGS. 18A-18B are graphs of measured "as-made" ionic conductances (S) and the effective conductance at gate controlled regions ($S_{GC}$) according to an aspect of the present invention.
Figure 18B:
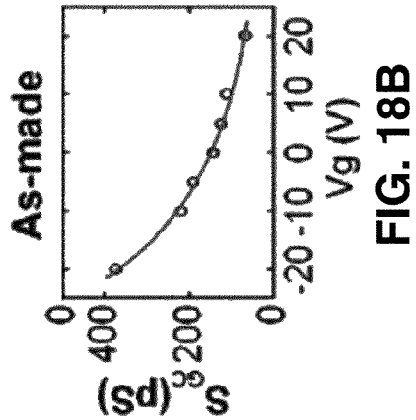
Figure 25:
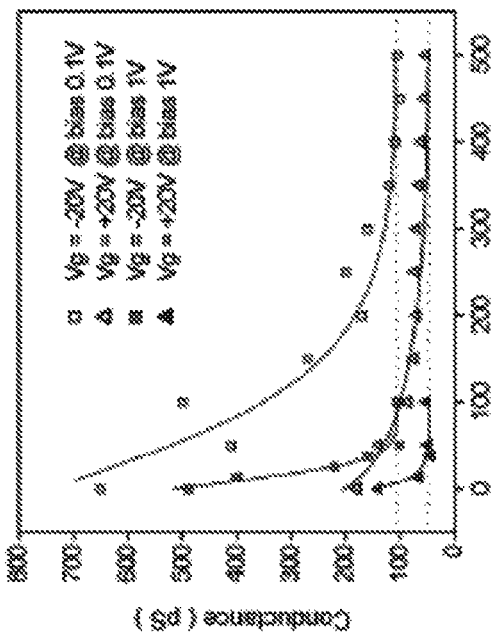
FIG. 25 is a graph of transient responses of ionic conductance when turning on the gate voltages according to an aspect of the present invention.

FIG. 18A through FIG. 21B illustrate ionic conductance aspects with respect to functionalization time. FIG. 18A and FIG. 19A illustrate that ionic conductance is more profound and provides a fairly stable field effect modulation, while it is subject to lower noise levels compared to as-made devices.

Figure 20A:
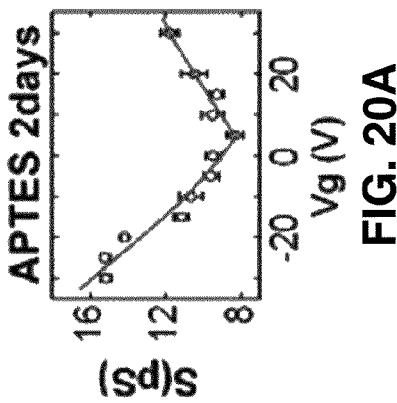
FIGS. 20A-20B are graphs of measured "APTES 2 day" ionic conductances (S) and the effective conductance at gate controlled regions ($S_{GC}$) according to an aspect of the present invention.
Figure 20B:
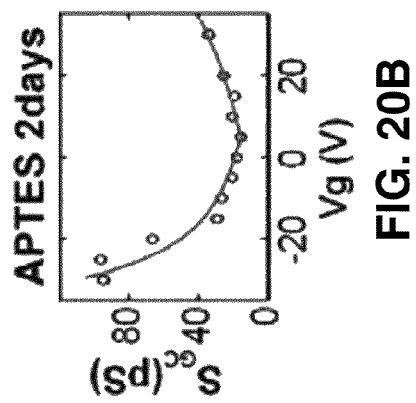
Figure 19A:
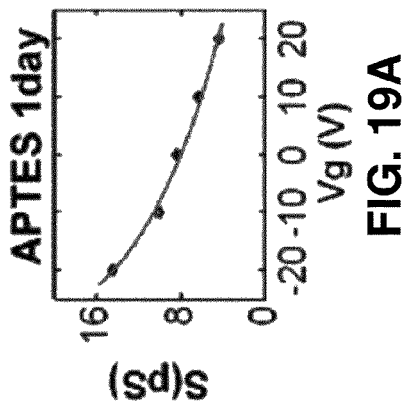
FIGS. 19A-19B are graphs of measured "APTES 1 day" ionic conductances (S) and the effective conductance at gate controlled regions ($S_{GC}$) according to an aspect of the present invention.
Figure 19B:
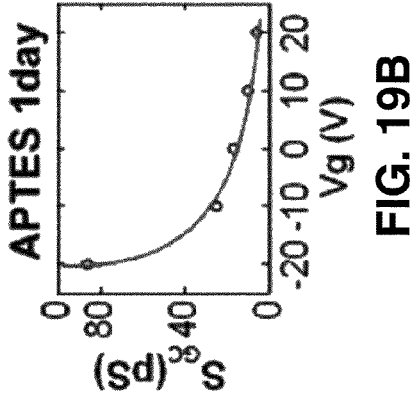

FIG. 20A is a graph which illustrates that two days of APTES functionalization resulted in ambipolar transport behavior. Negative gate voltage increased conductance significantly due to enhancement of cation as in p-FETs. A positive Vg of 5V slightly decreased conductance due to the depletion of cations, but when Vg was above 5V, ionic conductance again increased as one would expect for n-FETs. This observation is attributed to surface charge reversal after passing the ambipolar point. Under large positive gate voltage (e.g., Vg>5V), anions became the majority carrier resulting in n-FET characteristics. It will be appreciated that within semiconductor systems, small band gap materials tend to exhibit more profound ambipolar behavior. Nanofluidic transistors, in which both cation and anion densities are associated with the same electrical potential level, are essentially gapless transport systems. Consequently, ambipolar behavior would be expected once the inherent carrier concentration falls into suitable low concentration regime.

FIG. 21A is a graph indicating that the polarity of the nanotube ionic transistors can be completely reversed after a long period of surface modification. For example, in the graph of FIG. 21A four days of APTES treatment converted as-made p-FETs into n-FETs. Within the experimental range of Vg, conductance increased monotonically with increasing Vg. For all n-FET devices, the conductance at zero Vg is always lower than that for as-made nanotube devices, yet greater than that for the devices after one or two days of APTES treatment. This polarity switching is highly reproducible in various devices and by using different APTES concentrations.

FIGS. 18B, 19B, 20B and 21B depict gate electrode control ($S_{GR}$) in a nanofluidic transistor according to the invention, wherein regions that were not covered by gate electrodes, as shown in FIG. 13, resulted in series resistance. The effective conductance under gate electrode control ($S_{GR}$) was obtained for the as-made transistors and all functionalized transistors after abstracting series resistances. Gate electrode control, $S_{GR}$, was found to exhibit up to a ten-fold field effect modulation according to these tests. The region of a nanotube underneath a single gate electrode, such as approximately 4 μm wide, is as small as about 8 attoliter. The rapid and reversible modulation of ionic concentration or even local switching of the carrier polarity in such a small volume might represent the finest control of ion distribution which is available at this time within fluidic systems.

Field effect modulation in metal-oxide-semiconductor (MOS) systems relies on capacitive coupling between metallic gates and semiconductors. Capacitive coupling also plays a key role in our metal-oxide-solution (MOSol) systems. A three capacitor model was proposed by van den Berg et al. (refer to R. B. Schasfoort, S. Schlautmann, J. Hendrikse, and A. van den Berg, Science 286, 942 (1999)) to semi-quantitatively explain the relationship between gate voltage and $\zeta$ potential change in flow FETs.

FIG. 22 illustrates $\zeta$ potential change with respect to gate voltage for the present invention. The inset schematic depicts Cox, CST and CDL representing series capacitances of the silica nanotube wall, the compact layer and diffuse layer, respectively. Since the compact layer is very thin (<1 nm) and has a large dielectric constant (e.g., ~80) as in aqueous solutions, CST is thus very large and therefore negligible when connected in series with Cox and CDL. Accordingly, the $\zeta$ potential change ($\Delta\zeta$) can be calculated by $\Delta\zeta=$(Cox/CDL) Vg. This model predicts a linear relation between $\zeta$ potential and gate voltages. The value for $\Delta\zeta$ could be as large as 200 mV at Vg=20 V. In order to find out the experimental values of $\zeta$ potential and surface charge density, Possion-Boltzmann equations were used to numerically solve for the potential and ion distributions across the nanotube as a function of $\zeta$ potential. Integration of the anion and cation densities in the whole nanotube yields conductance enhancement factor as a function of $\zeta$ potential and surface charge density.

FIG. 22 and FIG. 23 depict estimated $\zeta$ potential and surface charge density. This estimate was based on comparing theoretical and experimental conductance enhancement factor, effective conductance (SGR), over the conductance of bulk solution if confined in the same volume to arrive at corresponding $\zeta$ potential and surface charge density. It turns out that $\zeta$ potential changes with Vg almost linearly, in agreement with the prediction of the three capacitor model. In contrast to its prediction that field effect modulation of $\zeta$ potential is concentration independent, the $\zeta$ potential modulation is greater in low inherent $\zeta$ potential devices (low "doping" level). The observed $\zeta$ potential changes between Vg=−20V and +20V range from ~1 $k_B$T/e to 5.5 $k_B$T/e, which is smaller than the theoretical value 200 mV (7.8 $k_B$T/e). This discrepancy may be attributable to the effective distance of the EDL diffuse layer which varies with surface potential and is not simply equal to Debye length.

Effective surface charge densities with respect to Vg are shown in FIG. 23. As-made p-type nanofluidic transistors exhibit four-fold field effect modulation of surface charge density. The "APTES 1 day" device has greatly reduced inherent surface charge density, and exhibits increased field effect modulation, such as about ten-fold. The n-type FET exhibits five-fold field effect modulation and lower inherent surface charge density (at Vg=0 V) compared to as-made p-type FETs. This difference might arise from the different deprotonation/protonation constants of the hydroxyl group as compared with the amino group. The ambipolar device exhibits a surface charge density switch from negative to positive when Vg exceeds approximately 5V. Theoretically, the surface charge density must be reduced down to zero to completely turn off the fluidic transistor. The experimental data shows large OFF state conductance and charge density, possibly due to the existence of parasitic conductance at the bottom side of nanotubes, which is not wrapped by metallic gate electrode and does not necessarily respond to applied gate voltage.

Figure 24:
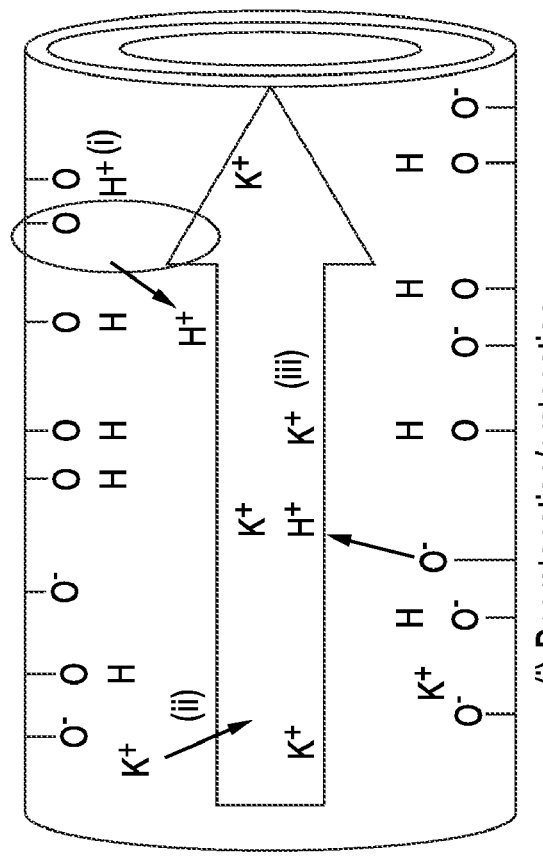
FIG. 24 is a schematic of surface chemical reactions and electrokinetic effect involved in field effect modulation according to an aspect of the present invention.

FIG. 24 illustrates basic kinetic processes at work within the nanotube of the nanofluidic device. In testing the present invention, the kinetic process of field effect control in a nanofluidic transistor has been examined. By way of example, consider a hydroxyl group terminated silica nanotube filled with KCl solution. Upon application of a gate voltage the three basic kinetic processes of FIG. 24 are shown comprising: (i) deprotonation or protonation in response to the external electrical field, (ii) adsorption or desorption of counter ions in compact layers; and (iii) ion exchanges between the transiently generated counter ions and bulk solution in microfluidic channels leading to a steady state of ion distribution. These tests illustrate that ionic conductance jumps in response to turning on the gate voltage, because of transient accumulation of the ions induced by surface reaction (i) and/ or (ii). This level of conductance then decays gradually down to steady states (dashed line). At the same gate voltages, high bias sweeping leads to rapid decay (relaxation time less than 60 seconds at 1V) while low bias gives slow decay (relaxation time of about 250 seconds at 0.1V). Such strong bias dependence was observed for both a negative and positive Vg. When the bias was swept between ±5V, conductance reached steady state immediately in a single I/V scan (10-20 sec). However, it was found that at the same bias, different gate voltages did not result in substantially different transient responses. Hence, the ion exchange step is believed to control the kinetics of field effect modulation in nanofluidic transistors. Faster field effect operation is expected in response to further reducing the nanotube dimension and increasing bias currents.

2.3 Method of Controlling Molecular Flow

The above examples discuss apparatus for controlling molecular flow in a fluid. It will be appreciated that these aspects of the invention also describe one or more methods for controlling molecular flow. Generally, the method involves the following principle steps. First, an inorganic nanotube is configured for communicating ionic fluid between a first end (e.g., source) and a second end (e.g., drain). Electrodes are coupled to the first and second ends of the nanotube, with a gate electrode positioned proximal the nanotube (preferably fully or partially surrounding the nanotube). A bias current is established between the first end and second end which passes through the ionic fluid in the inorganic nanotube. Ionic movement through the nanotube is then controlled in response to the level of applied gate voltage, thus a fluidic transistor structure is formed.

The nanotube is preferably adapted with a small diameter to assure that an electrical double layer (EDL) forms whose diffuse layer extends sufficiently into the interior of the nanotube to control movement. Preferably, the diffuse layer extends to the center (or overlaps the center) which results in full control of movement across the whole cross-section of the nanotube. It will be appreciated that in tubes of larger diameter (e.g., above about 50-100 nm) the diffuse layer will be unable to direct molecular movement at the center of the tube. Molecular control can be increased or altered by functionalizing the nanotube. An example above was the exposure to APTES over a desired preparation time, though other forms of functionalization can be utilized without departing from the teachings of the present invention. In its most basic form, functionalizing provides for the selective control of the movement of anions, cations, or both anions and cations through the nanotube thus making n-type, p-type or ambipolar fluidic nanotransistors.

3. Nanotube Device Fabrication.

Figure 26:
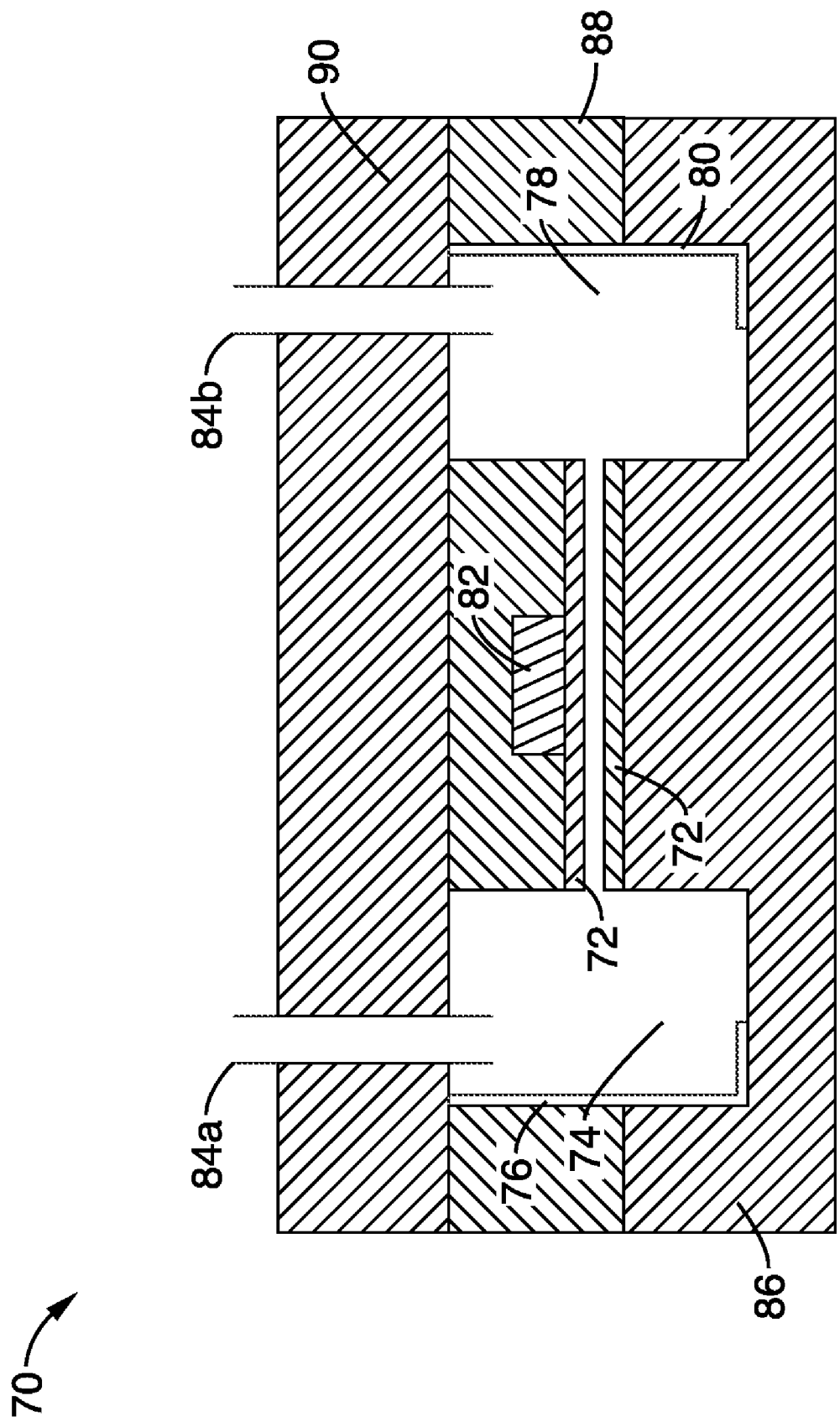
FIG. 26 is a cross-section of an inorganic nanotube nanofluidic transistor according to an aspect of the present invention.

FIG. 26 illustrates an example embodiment 70 of an inorganic nanotube nanofluidic transistor. A nanotube 72 (e.g., single silica nanotube) is shown fluidly coupled between a source volume 74, incorporating electrode 76, and a drain volume 78, incorporating electrode 80. It should be appreciated that the terms "source" and "drain" are adopted above in response to the electrical characteristics which are an analog of a MOSFET device, and not in response to a limitation on the direction of fluid flow, such as indicative of flow originating from source and moving into the drain. A conductive gate 82 (e.g., chromium) is shown proximal (e.g., adjacent, partially surrounding, or fully surrounding) at least a portion of nanotube 72. Access holes 84a, 84b are shown for communicating fluid to the source and drain regions. By way of example and not limitation, the base portion of the nanofluidic transistor comprises a quartz substrate 86, while the upper portion 88 comprises one or more layers of $SiO_2$, such as deposited by chemical vapor deposition (CVD).

The transistor shown has been fabricated by two separate steps, specifically chemical synthesis of silica nanotubes 72 for nanofluidic channels and integration with lithographically defined microfluidic channels 74, 78. In this example, silicon nanowires were synthesized and oxidized in dry $O_2$ at 850° C. for 1 hour to form a 35 nm silica sheath. To avoid photoresist filling into the nanotubes, the as-made $Si/SiO_2$ core-sheath nanowires were left sealed instead of etching through the Si cores to form $SiO_2$ nanotubes until all the surface device structures had been fabricated. After dispersion of $Si/SiO_2$ nanowires onto quartz substrates, a 100 nm Cr metal layer was sputtered onto the substrates, and subsequently etched with photolithography defined photoresist etching mask to form Cr lines above the $Si/SiO_2$ nanowire serving as gate electrodes 82. Then a 2 μm thick low temperature oxide 88 was deposited on the entire substrate 86 using low-pressure chemical vapor deposition (LPCVD) with $SiH_4$ chemistry and then densified by annealing in inert gas at ambient temperature. Two microfluidic channels are patterned and etched to connect to each of the ends of $Si/SiO_2$ nanowires. Two metal lines (e.g., Pt or Ag) were patterned on both sides of the nanowire as source and drain electrodes. It is also convenient and practical from a testing perspective to simply insert two Ag/AgCl electrodes into the access holes to serve as source/drain electrodes. Finally the silicon core of the nanowire was etched away using $XeF_2$ to form the silica nanotube.

The resulting devices were bonded with a PDMS cover in which access holes had already been drilled. Before bonding, device chips were cleaned with oxygen plasma at 200 W for one minute and immersed in DI water to form hydrophilic surfaces in microfluidic channels which facilitate the aqueous solution injection during experiment. The device chips were taken out and dried utilizing a nitrogen gun. A piece of fresh PDMS cover with access holes was cleaned in isopropanol (IPA) for three minutes assisted by ultrasonic treatment. Finally, the PDMS cover was aligned and pressed onto the device chip to complete the bonding process. Measurements were conducted typically one to three days after bonding.

3.1 Electrical Measurements.

Electrical measurements for an implementation of the device shown in FIG. 26 were carried out. By way of example and not limitation, electrical testing of the device was conducted in a Faraday cage having a common ground with all the measurement equipment. Current-voltage (I-V) characterization was carried out with a source measure unit. Gate voltage was supplied with a voltage source generating up to 100 V. The measurement system was controlled with lab-based software and data was collected through an IEEE-488 interface. A rise time of 33 μS was set for all these tests. Data collection in this test setup was carried out with a PC-based data acquisition system (e.g., in this case having a maximum sampling rate 100,000 samples/Second). Silver or silver-chloride (Ag/AgCl) electrodes were used as source and drain electrodes in these tests except for the deionized (DI) water conductance measurements in FIG. 27 and FIG. 28 for which inert platinum (Pt) electrodes were used to avoid contamination. All the electric measurements were conducted in a clean room to avoid dust contamination.

3.2 Surface functionalization with APTES.

By way of example and not limitation, the interior of the nanotube was functionalized with an APTES solution. The APTES solution can be prepared by adding 2% (vol) APTES liquid (Aldrich) to acetone, which was pre-dried overnight using 4-8 mesh (4A pore size) molecular sieves. The as-fabricated device chips were cleaned with oxygen plasma and dried at 100° C. in a convection oven for about 20 minutes prior to PDMA cover bonding. Then the chips were immersed in APTES acetone solution for a desired time with the reaction container capped to prevent introduction of moisture. After functionalization, the device chips were rinsed with dry acetone a couple of times and then left in acetone overnight. Finally, PDMS cover bonding was conducted in a similar way as described previously, although it took only 30 seconds of oxygen plasma cleaning at 100 W. It will be appreciated by one of ordinary skill in that art that these process steps can be alternatively implemented in a number of different ways.

3.3 Scanning Electron Micrographs of Devices.

Figure 28:
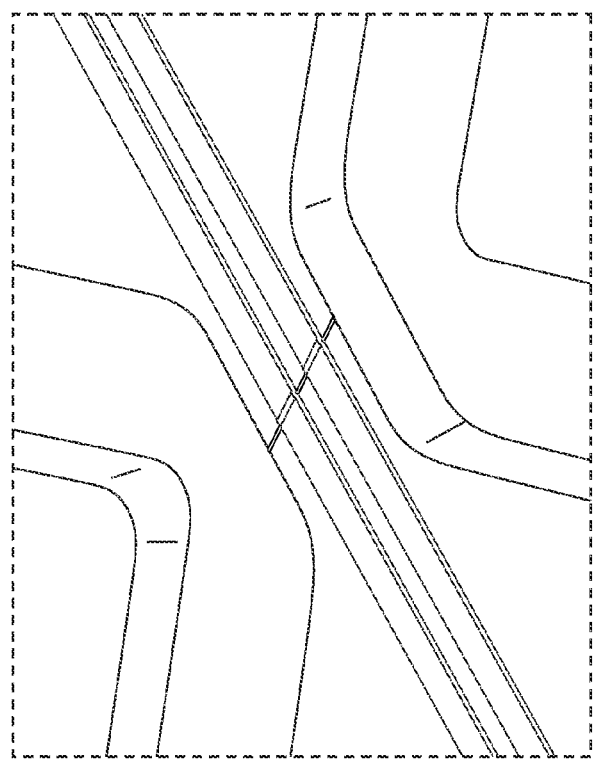
FIG. 28 is a rendering of a FESEM image showing magnified details of the nanofluidic transistor device shown in FIG. 26.
Figure 27:
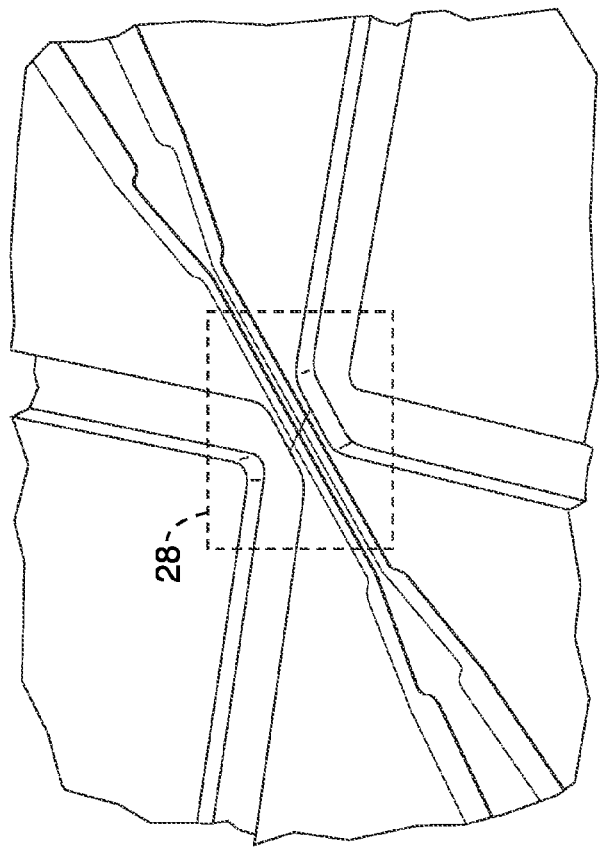
FIG. 27 is a rendering of a FESEM image of the nanofluidic transistor device shown in FIG. 27.

FIG. 27 and FIG. 28 are renderings of a field emission scanning electron microscopy (FESEM) characterization of the as-fabricated nanofluidic transistor before PDMS cover bonding. These example embodiments show the structure of microfluidic channels at both sides bridged by a single silica nanotube which is embedded underneath an LPCVD $SiO_2$ layer. Metal gate electrodes which are also embedded in the $SiO_2$ layer are visible topographically in the renderings of the FESEM images.

3.4 Unipolar Ionic Distribution and Transport in Silica Nanotubes.

Figure 29:
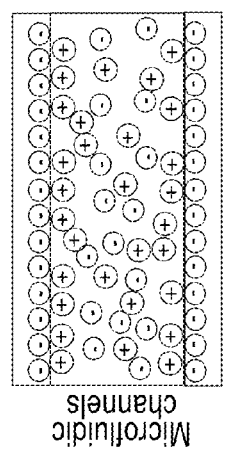
FIG. 29 is a schematic of ion distribution for a silica microfluidic channel according to an aspect of the present invention.
Figure 31:
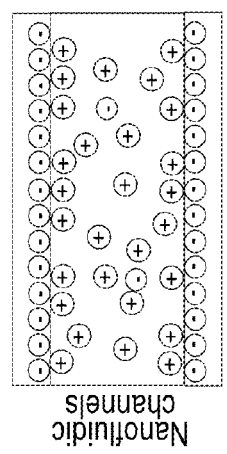
FIG. 31 is a schematic of ion distribution for a silica nanofluidic channel according to an aspect of the present invention.

FIG. 29 through FIG. 32 illustrate ion distribution and electric potential diagrams for silica microfluidic channels and nanofluidic channels. These figures qualitatively describe the difference between microsized (FIGS. 29-30), and nano-sized (FIGS. 31-32) fluidic systems and the formation of unipolar ionic environments when shrinking channel size to approach the Debye screening length. A schematic example of ionic distribution within a microfluidic channel is depicted in FIG. 29, which contrasts in character with the ionic distribution of the nanofluidic channel depicted in FIG. 31. In comparing FIG. 31 with FIG. 29 it can be seen that the relative availability of mobile negative ions in the nanofluidic channel of FIG. 31 in comparison with FIG. 29. The nanofluidic channels thus are capable of taking advantage of EDL effects. Potential and ionic concentration are shown compared between the microfluidic channel in FIG. 30 in comparison with the use of the nanofluidic channel of FIG. 32. Through these diagrams one can clearly discern the unique characteristics of the nanofluidic channels which are beneficially utilized according to the different aspects of the present invention.

Figure 33:
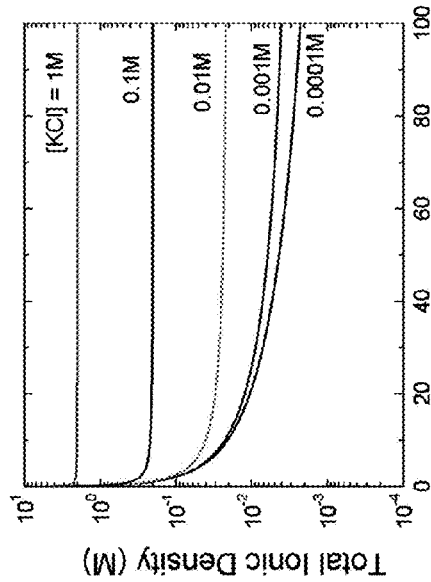
FIG. 33 is a graph of a theoretical calculation of total ionic density at the nanotube size according to an aspect of the present invention.

FIG. 33 is a graph of a theoretical calculation of the total ionic density (cation and anion) as a function of nanotube size, based on the simple principle of charge neutrality, wherein surface charge density was assumed to be 0.01 $C/m^2$. Simulation results clearly indicate two profound trends in the data. First, decreasing nanotube diameter leads to more enhanced total ionic density inside nanotubes, which is essentially the cations which are required to balance the negative surface charge at the silica nanotube surface. Smaller nanotubes squeeze the cations and increase the real ionic density to form a unipolar carrier (ion) profile inside nanotubes. Secondly, low concentration ionic (<0.01 M) solution tends to readily form a unipolar environment inside the nanotube, while the high concentration solution (>0.1 M) only shows slight enhancement in very small nanotubes. The meagerness of this change is due to low ionic strength solutions having larger Debye screening length which allows significant extension of surface charge effect across entire nanotubes.

Figure 34:
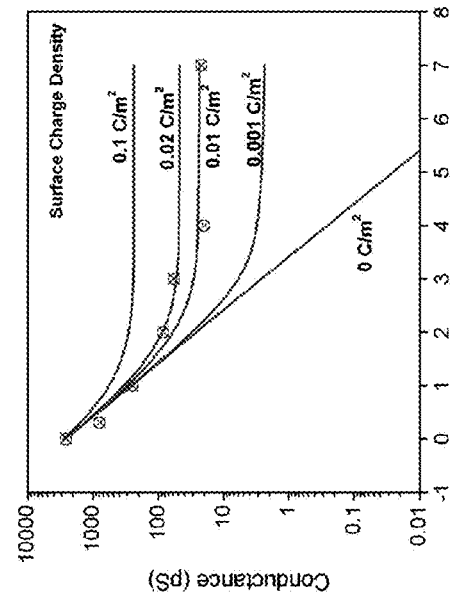
FIG. 34 is a graph of experimental data of KCl salt concentration dependence of the ionic conductance in a single silica nanotube nanofluidic transistor according to an aspect of the present invention.
Figure 30:
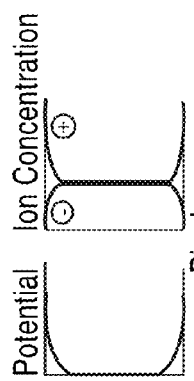
FIG. 30 is a graph of electric potential for the silica microfluidic channel of FIG. 29.
Figure 32:
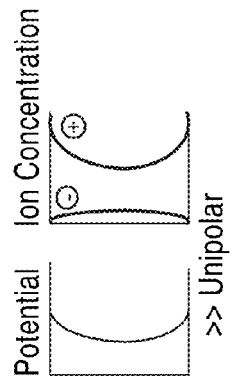
FIG. 32 is a graph of electric potential for the silica nanofluidic channel of FIG. 31.

FIG. 34 is a graph of experimental data of KCl salt concentration dependence of the ionic conductance in a single silica nanotube nanofluidic transistor which clearly shows deviation from microfluidic system prediction (0 $C/m^2$ line) and confirms the formation of unipolar ionic conduction at low concentration (<1 mM). A high concentration solution in the nanotube essentially behaves like bulk salt solution in microfluidic systems due to very short Debye screening length (<3 nm for [KCl]>0.01 M).

3.5 Calculation of $\zeta$ Potential and Charge Density.

The ionic concentration is given by the Boltzmann distribution:

$$n_{+(-)} = n_0 \exp\left(\frac{\mp e\varphi}{k_B T}\right) \tag{4}$$

where $n_{+(-)}$ denotes the real cation and anion density, respectively, inside a nanotube where electrical potential is $\varphi$. The value no denotes the cation or anion density at $\varphi=0$, which equals the bulk KCl concentration, $K_B$ is the Boltzmann constant, T is absolute temperature, e is the electron charge. Total ionic density n (both cations and anions) is given by:

$$n = n_0 \exp\left(\frac{-e\varphi}{k_B T}\right) + n_0 \exp\left(\frac{e\varphi}{k_B T}\right) = -2n_0 \cosh\left(\frac{e\varphi}{k_B T}\right) \tag{5}$$

The net charge density $\rho$ is $$\rho = n_0 \exp\left(\frac{-e\varphi}{k_B T}\right) - n_0 \exp\left(\frac{e\varphi}{k_B T}\right) = -2n_0 \sinh\left(\frac{e\varphi}{k_B T}\right) \tag{6}$$

The Poisson equation for the electric potential is:

$$\nabla^2 \varphi = \frac{-e\rho}{\varepsilon_w} = \frac{2n_0 e}{\varepsilon_w} \sinh\left(\frac{e\varphi}{k_B T}\right) \tag{7}$$

where $\varepsilon_w$ is the electrical permissivity of the aqueous solution.

In a symmetric system (cylindrical nanotubes), the boundary condition in the center is given by:

$$\left.\frac{d\varphi}{dx}\right|_{x=0} = 0 \text{ which gives} \tag{8}$$

$$\left(\frac{d\Phi(x)}{dx}\right)^2 = 4S_n^2[\cosh(\Phi(x)) - \cosh(\Phi(0))]$$

Herein, value x is the coordinate across the center of the nanotube which is the origin. Value x is normalized with radius R of the nanotube, such that $0 \leq x \leq 1$. For simplicity, $\varphi(x)$ is also nondimerized by $$\Phi(x) = e\varphi(x)/k_B T.$$

$\Phi(0)$ is calculated by integration of $\Phi(x)$ from $\zeta$ to $\Phi(0)$, and x from 1 to 0 in Eq. (8). Then $\Phi(x)$ can be numerically solved by integration from $\Phi(0)$ to $\Phi(x)$ while x varies from 0 to x.

Once the potential diagram $\Phi(x)$ is solved for various zeta potentials ($\zeta$), then the Boltzmann distribution can be further utilized to calculate ionic concentration for both cations and anions. The relation between surface charge density and zeta potential ($\zeta$) is calculated based on the total charge neutrality.

$$\sigma = \frac{1}{2\pi RL} \int_0^1 2\pi x L \rho(x) dx = -\frac{1}{R} \int_0^1 2xn_0 \sinh(\Phi(x)) dx \tag{9}$$

For the sake of simplicity, it is assumed that the mobilities for $K^+$ and $Cl^-$ are equal, wherein the enhancement factor is defined as the measured conductance in the nanotube over the ideal conductance in bulk solution if it is confined in the same volume $(S/S_0)$, given as:

$$S/S_0 = \int_0^1 2\pi x(n^+ + n^-)/(2n_0) dx = \int_0^1 2\pi x \cosh(\Phi(x)) dx \tag{10}$$

For various zeta potentials ($\zeta$), one can numerically compute a set of $S/S_0$ values according to Eqs. (8) and (10). Then based on experimentally measured enhancement factor $(S/S_0)$, zeta potentials can be back-extracted. Eq. (9) represents the correlation between surface charge density $\sigma$ and $\zeta$, wherein surface charge density $\sigma$ can be calculated from $\zeta$ once it is known.

Nanofluidic systems have been described which incorporate inorganic nanotubes for the sensing and/or controlled transport of ions, molecular species, and biochemical species (e.g., DNA). Implementations are described for sensing the flow of DNA in response to translocation through the nanotube. In addition, fluidic transistor implementations are described which allow for controlling the movement of either or both ionic polarities in response to applied gate voltage. In either case, the nanotube interior can be modified, such as functionalized, to alter specificity of flow or ionic characteristics. Fabrication details were described by way of example and not limitation throughout the preceding specification. One of ordinary skill in the art will appreciate that numerous variations and modifications can be incorporated within these nanofluid devices without departing from the teachings herein.

Functionalization of Nanofluidic Channels

Figure 35:
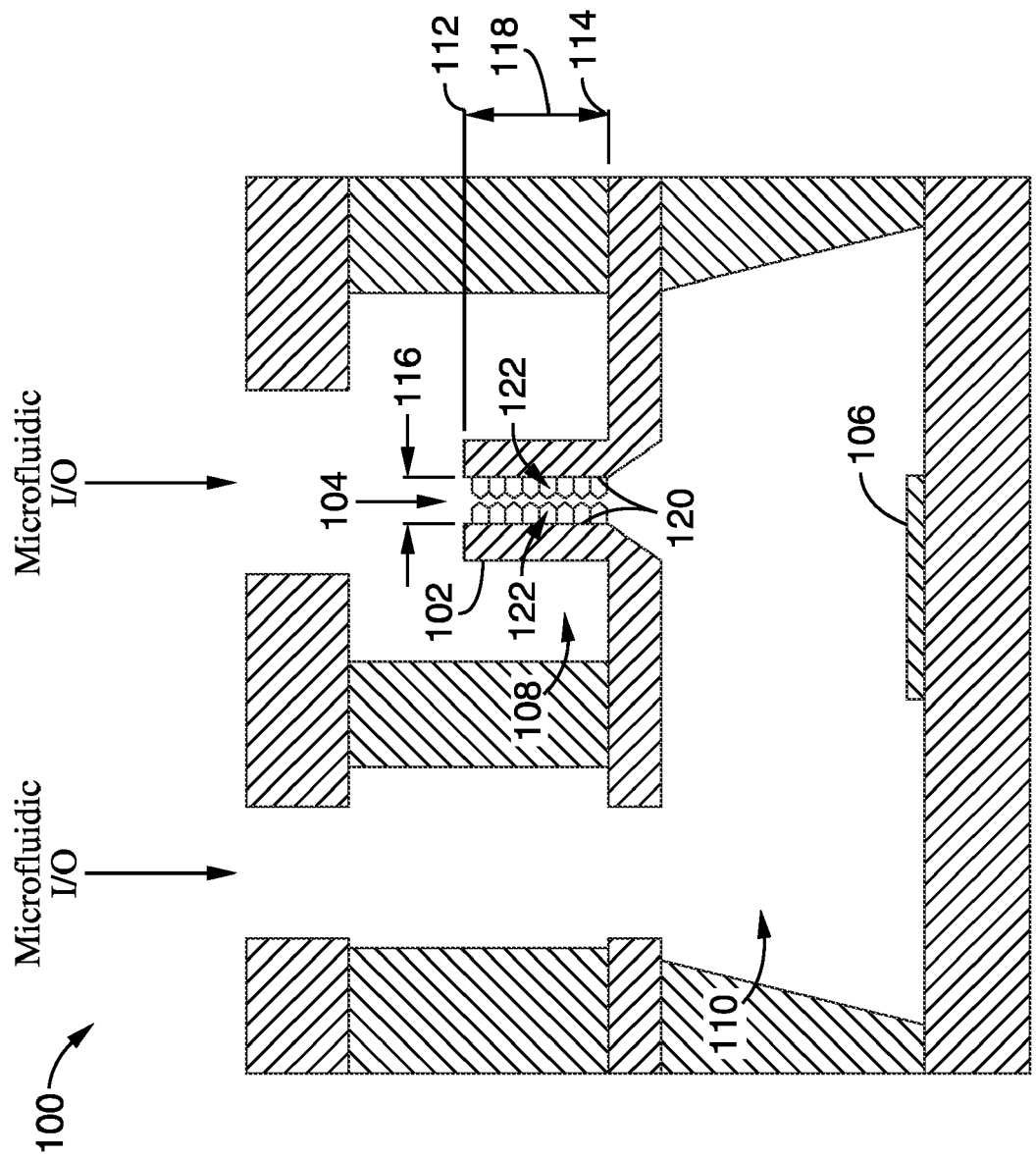
FIG. 35 is a schematic of a microfluidic system with a nanochannel according to the present invention.

Referring to FIG. 35, a schematic of one embodiment of a nanofluidic device 100 comprising at least one nanotube 102 with an inner channel 104 and a means 106 for determining conduction of the nanotube 102 is shown. The schematic also shows a source reservoir 108 and a sink reservoir 110 interconnected by nanotube 102. Although reservoirs 108, 110 are shown, it will be understood that the reservoirs may also be microchannels or other fluid channel. The nanotube 102 may also be an etched channel and part of a plurality of nano-scale tubes that form an array of tubes or pores fluidly connected to a system of microchannels and reservoirs. Nanotubes in the array may be arranged in series or in parallel and may vary in length and diameter. A single nanotube 102 is shown for illustration purposes.

It will be appreciated that a central component of devices fabricated from fluidic nanotubes 102 are the nanotubes themselves. Nanotubes 102 can be fabricated according to various methods known in the art and can have various compositions of matter. While fluidic devices can be made using carbon-based nanotubes, such nanotubes are generally hydrophobic and may be unsuitable for fluidic applications without modification and therefore non-carbon based nanotubes are preferred. It is also preferred that the non-carbon-based nanotube 102 be non-porous (e.g., having a seamless tube wall) for use in fluidic applications. The tubular nanotube 102 illustrated in FIG. 1 has a first end 112 and a second end 114, a channel diameter 116, a length 118, and non-porous inner walls 120.

Fluid flow and chemical reactions that take place in nanometer scaled structures are fundamentally different than take place in larger scale channels, because the molecules involved are approximately equal to the dimensions of the nanotube in which the reactions occur. The unique properties of nanochannels arise when the nanochannel size is comparable to either of two length scales: (a) the range of electrostatic interactions in solution and (b) size of the analyte molecules. Since biomolecular analytes are typically charged and have sizes comparable to the above length scales, variable ionic conditions have a predictable effect on the transport characteristics of nanochannels in the presence of biomolecular charge and size of the analyte.

It has been shown that a solid surface such as inner walls 120 in contact with an ionic solution is often charged due the presence of ionized surface groups or adsorbed ions. Counterions in solution accumulate near this charged surface and co-ions are repelled, shielding the surface charge in a characteristic distance known as the Debye length. The Debye length, $I_D$, characterizes the distance of ionic interactions in solution and can be made to span the range $1\,\text{nm} \leq I_D \leq 100\,\text{nm}$ by adjusting the ionic concentration of the buffer solution. Accordingly, in microchannels, the Debye length is usually much smaller than the channel dimensions and the bulk of the solution is shielded from the surface charge. When the channel size is smaller than the Debye length and the nanochannel surface is charged, the channel becomes a unipolar solution of counterions at a concentration that neutralizes the surface charge. The co-ions are essentially repelled from the channel. It is therefore possible to create conditions in nanotube 102 where the electrical double layer confined to the inner walls 120 or ranging out into the channel 104.

Within the Debye layer, the surface charge controls ionic concentrations, which in turn affect the nanochannel conductance that can be calculated for a given surface charge or potential. When a 1:1 electrolyte at a bulk concentration of n molecules/m is introduced in a nanochannel of height 2h and surface charge σ, the conductance deviates significantly from that of bulk electrolyte when σ/eh is comparable to n; that is, when the effective concentration of ions required to neutralize the surface charge, σ/eh, is comparable to bulk ion concentration, n, surface charge plays an important role.

In the regime of low electrolyte concentration, σ/eh>>n, surface charge governs the ionic concentration inside the channel to maintain electroneutrality ($n_\pm = \sigma/eh$), which in turn controls the nanochannel conductance. Generally less than 1M ionic solutions are within the low regime. Thus the nanochannel conductance (G) for a 1:1 electrolyte, neglecting electroosmotic effects is given by the equation:

$$G = 2\sigma \frac{\mu_{+/-} w}{l}$$

In this equation, the symbol μ is ionic mobility (subscripts denote cation/anion) and w and l are the channel width and length, respectively. Hence, any functionalization of nanochannel surfaces with different surface groups and biomolecules can be expected to change surface charge and the nanochannel conductance. A signature of this regime is that conductance becomes independent of bulk ionic concentration as well as the channel height.

In the high concentration regime, σ/eh, n and conductance becomes largely independent of surface charge. In this regime, conductance depends on channel height and increases linearly with ionic concentration, as shown by the following equation:

$$G = 2neh\frac{(\mu_+ + \mu_-)w}{l}$$

If the size of the biomolecules in the channel is comparable to the channel size, the resulting change in channel geometry (h) would result in a change in nanochannel conductance.

Consider a biomolecule with charge q and volume V present in a solution with ionic concentration n in the nanochannel. The number of charges on the biomolecule is q/e, where e is the charge of an electron. The number of conducting ions introduced due to biomolecule charge is expected to be of the order of q/e, while the number of excluded ions is of the order of nV. These contributions are analogous to the equations described above with the first contribution depending only on charge and the second one varying with geometry and ionic concentration. The biomolecule charge effect dominates at lower ionic concentration, but as the ionic concentration increases, the number of ions displaced due to the biomolecule volume increases. This exactly offsets the effect of biomolecule charge at a certain concentration, i.e., when n~q/eV. At higher concentrations, the volume exclusion effect dominates.

Hence, in both the high and low concentration schemes, measurement of electrical conductance of nanochannels offers means of probing biological reactions and modifications on surfaces. In the past, electrokinetic measurements in microslits have been used for the characterization of surfaces and measurement of protein adsorption. However, electrokinetic characterization is often cumbersome, involving the application of pressure and the measurement of flow rates. In nanochannels, surface effects dominate and we can expect biological modifications and reactions to be detected directly by simply measuring the conductance.

It can be seen, therefore, that the surfaces of inner walls 120 of nanotube 102 can be functionalized with immobilized biomolecules 122, for example, and detect conductance changes and control the ionic and structural conditions of the channel 104 of the nanotube 102. Functionalization of the surfaces 120 could enable the detection of specific interactions and selective binding to target biomolecules with a very low sample size, even approaching single protein. Likewise, surface functionalization will allow charge sensitive biosensing and label free detection of binding events.

Immobilized biomolecules can also selectively alter the geometry of the nanochannel as well as allow the manipulation and selection of nanochannel environment for passive transport, segregation or sizing of ionic or molecular species through an array of nanochannels.

The electrical properties of the nanotubes are highly sensitive to surface charge transfer and changes in the surrounding environment. Accordingly, functionalization of the inner walls 120 may be accomplished with a wide variety of biomolecules and can be specifically tailored to a desired diagnostic procedure, assay or molecule. Such biomolecules may be receptors, ligands, peptides, oligonucleotides or may be inorganic.

Accordingly, nanochannel conductance can be used to sense surface charge and the presence of biomolecules immobilized on nanochannel surfaces in both surface-charge-governed and geometry-governed regimes. The devices provide for an integrated nanofluidic platform with a robust electronic probing scheme that is amenable to scaling and multiplexing. This technique is also useful for charge-sensitive biosensing, allowing label-free detection of binding of small molecules and kinase activity, which are difficult to detect conventionally.

Figure 36:
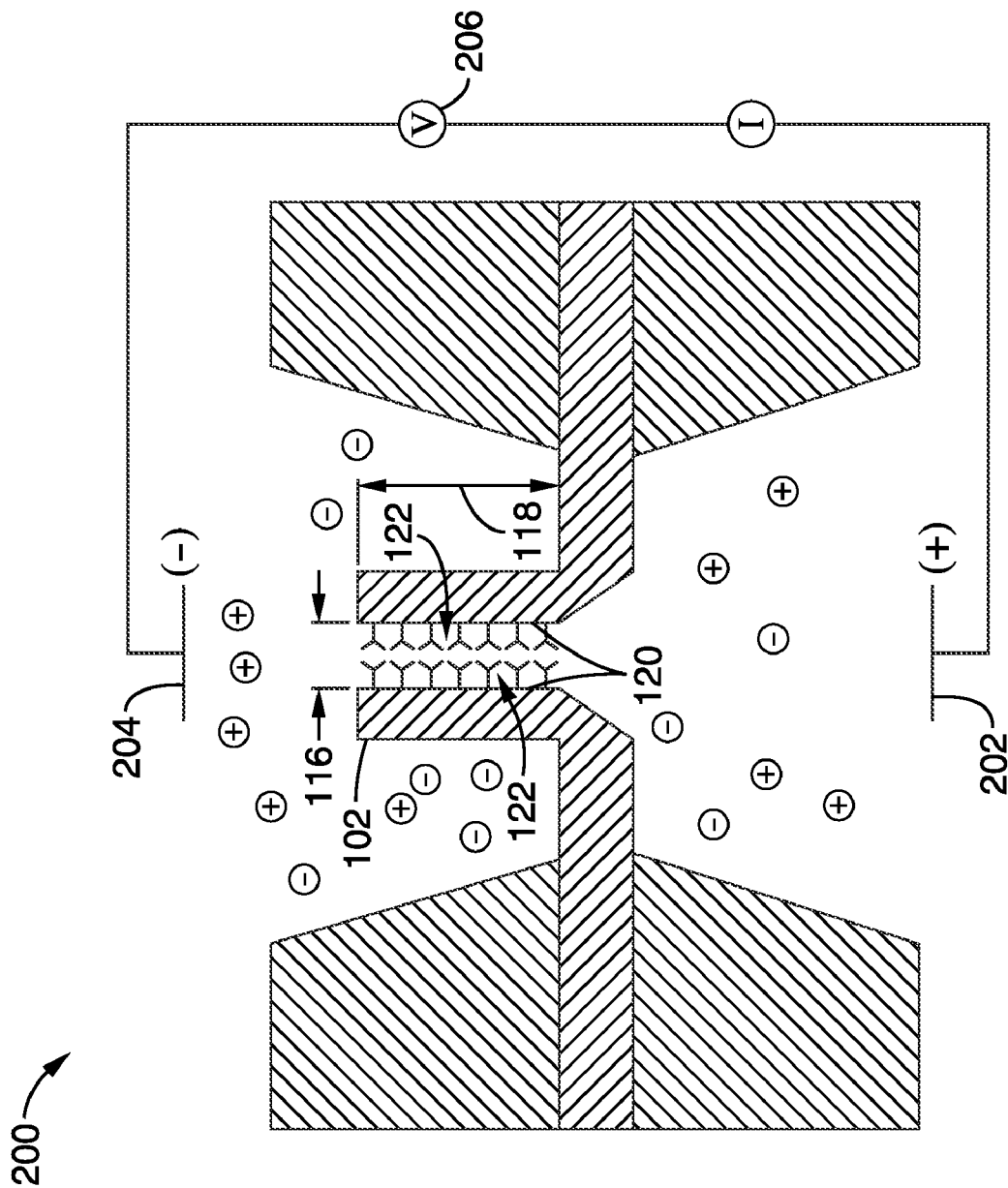
FIG. 36 is a schematic of a nanochannel according to another embodiment of the invention with electrodes providing electrical bias and generating ionic current.

In a second embodiment, shown schematically in FIG. 36, an apparatus 200 also includes at least one positive electrode 202 and at least one negative electrode 204 that are connected to a power source 206. Electrodes 202, 204 are preferably placed on opposite sides of the nanofluidic channels 104 for applying electrical bias and generating ionic current. A nanochannel 104 preferably has at least one dimension 116, 118 less than or equal to the Debye length so that electrostatic fields can penetrate throughout the channel enabling direct ionic or molecular manipulation using surface charge or field-effect in the nanotube 102.

In this embodiment, the ionic concentrations are both spatially and temporally controllable by electrostatic fields due to the microfabricated gate electrodes. By controlling the surface charge density in a region along the length of the channel, the ion current can be modulated, similar to modulation of charge transport in a field effect transistor due to a gate bias. This capability may be harnessed for applications such as isoelectric focusing of proteins and analyte stacking, while retaining the design flexibility of microfabrication and the controllability of gating voltage.

The devices with functionalized channels 104 could be part of various nanocapillary devices, including, but not limited to, field effect transistors, nanoelectrophoretic devices, detectors, DNA sequence detectors, immunosensors, tube-field-effect transistors, microfluidic wafers, nanocapillary wafers, electrode wafers, MEMS switching chips, sensors, thermoelectric devices, photonic devices, nanoelectromechanical actuators, nanoelectromechanical sensors, nanoscale fluidic bioseparators, imaging devices, and combinations thereof.

The invention may be better understood with reference to the accompanying examples, which are intended for purposes of illustration only and should not be construed as in any sense as limiting the scope of the present invention as defined in the claims appended hereto.

EXAMPLE 1

Conductance characteristics of nanofluidic channels (nanochannels) that can be selectively manipulated generally fall into two categories: at low ionic concentrations, conductance is governed by surface charge while at high ionic concentrations it is determined by nanochannel geometry and bulk ionic concentration.

Aminosilane chemistry and streptavidin-biotin binding were used to study the effects of surface reactions on nanochannel conductance at different ionic concentrations. Immobilization of small molecules such as aminosilane or biotin mainly changes surface charge, affecting conductance only in the low concentration system. However, streptavidin not only modifies surface charge but also occludes part of the channel, resulting in observable conductance changes in both low and high concentration schemes.

In order to demonstrate the effect of biomolecules on microchannel conductance, a nanochannel device was constructed. Fabrication of the nanochannel device began with a 30 nm thick layer of polysilicon deposited on a fused silica wafer using a low-pressure chemical vapor deposition (LPCVD) process and then subsequently patterned, forming sacrificial material that defined the nanochannels. Polysilicon film thickness was measured using a Nanospec 3000 film analysis system (Nanometrics) as well as with an Alpha-Step IQ surface profiler (KLA-Tencor) after patterning the thin film. A 2 μm thick low-temperature oxide was then deposited in a LPCVD process, annealed, patterned, and etched down to access the nanochannel ends.

Microchannels with access holes were fabricated on another fused silica wafer. The nanochannel and microchannel components were then bonded together using a transfer bonding technique with poly-(dimethylsiloxane) (PDMS) (Sylgard 184, Dow Corning) as an adhesive.

A number of staggered nanochannels were used in the fabrication process such that only one set of nanochannels bridged the microchannels. After bonding, nanochannels were formed by etching the sacrificial polysilicon with xenon difluoride gas at a pressure of 3 Torr for 1.5 hours. Once the channels were formed, the entire device was treated with oxygen plasma at 300 W for 10 minutes in a plasma etcher (Technics).

The plasma-treated surfaces of the channels were immersed in a 2% solution of (3-aminopropyl)trimethoxysilane (APT-MS) (Gelest, Inc.) in ethanol for 1 hour at room temperature, followed by a 5-minute ethanol rinse. The devices were then immersed in a 0.1×phosphate-buffered saline (PBS, pH 7.2, Invitrogen; 10×PBS is an aqueous solution of 1.55 M NaCl, 0.015 M $KH_2PO_4$, and 0.027 M $Na_2HPO_4$). Biotinylation of the surface was done by treating the aminosilane-coated surface with a 10 mM solution of Sulfo-NHS-SS-Biotin (sulfosuccinimidyl 2-(biotinamido)-ethyl-1,3-dithiopropionate) (Pierce Biosciences) in 0.1×PBS for 1 hour at room temperature. Under these conditions, the succinimide moiety reacts readily with the primary amine group of the APTMS resulting in cross-linking biotin to the surface. The NHS-SS-biotin cross-linker was used because of its long spacer arm, which reduces steric constraints leading to better binding efficiency of avidins. Residual amine groups, if any, were then passivated by treating the surface with a 10 mM solution of n-hydroxy-succinimide (NHS) (Sigma Aldrich) in 0.1×PBS for 1 hour at room temperature. (1×PBS corresponds to an ionic concentration of 0.15 M).

Following each step of surface reactions, electrical conductance of the nanochannels was measured at a range of buffer concentrations using a Keithley 6430 sub-femtoamp source meter controlled through a GPIB interface by a real-time control and analysis MATLAB program. Ag/AgCl electrodes were used to make electrical contact with solutions through access holes at the ends of microchannels. While solutions were changed, conductance measurements and rinses were carried out alternately to ensure complete rinsing.

Figure 37A:
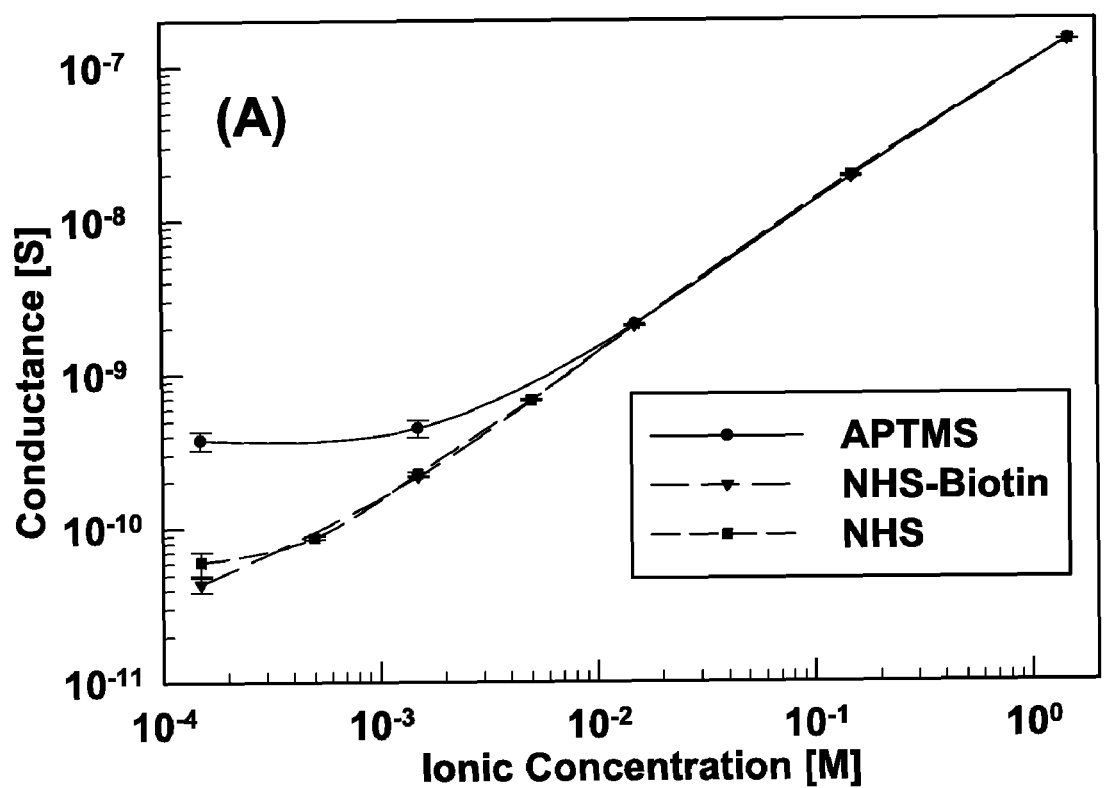
FIG. 37A is a plot of nanochannel conductance versus ionic concentration after various steps of surface functionalization.
Figure 37B:
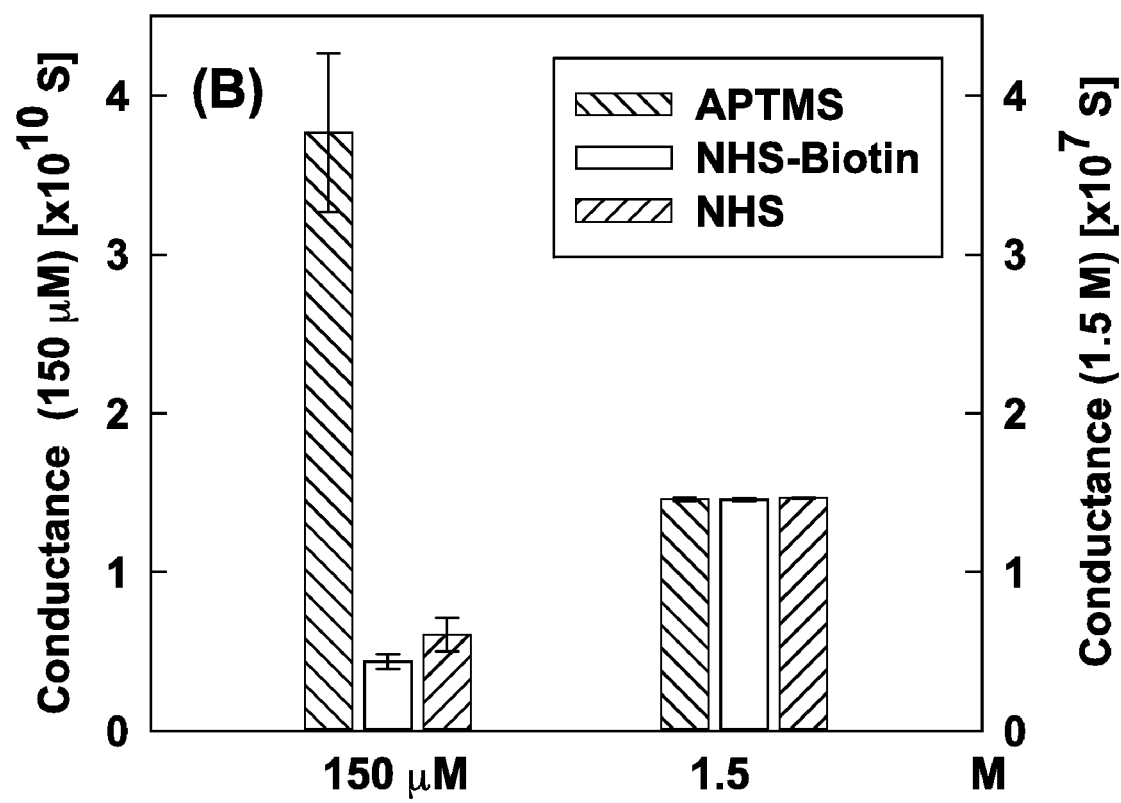
FIG. 37B is a detailed plot of conductance at the highest and lowest buffer concentrations.

Nanochannel conductance for a range of concentrations from 0.001× to 10×PBS after each step of surface modification was obtained. The microchannel device was first treated with APTMS, followed by NHS-SS-biotin and then NHS. Changes in nanochannel conductance after the various steps of surface functionalization of the channels at different buffer concentrations is shown in FIG. 37A and FIG. 37B. As seen in FIG. 37A, APTMS functionalization resulted in high conductance at low ionic concentrations. This conductance dropped to 11% of its original value upon treatment with NHS biotin. Subsequent treatment with NHS increased conductance slightly. No appreciable change in conductance was observed at high ionic concentrations indicating absence of steric blocking. FIG. 37B is a detailed plot of conductance at the highest and lowest buffer concentrations. The error bars correspond to five measurements at each point.

It was observed that at higher buffer concentrations, conductance varied linearly with concentration. Approximating 10×PBS as 1.55 M NaCl with an equivalent conductivity of $10^{-2}$ m²S/mol (or $\mu_+ + \mu_- = 10.4 \times (10^{-8}$ m²/V s)) and device geometry of 10 parallel 120 μm×3.5 μm×30 nm channels (first two dimensions estimated from micrographs), the expected conductance is calculated to be $1.35 \times 10^{-7}$ S, which is in reasonable agreement with the measured nanochannel conductance under the same conditions.

The conductance was repeatable from device to device, confirming the integrity of nanochannels and the microchannel interface. However, at low buffer concentrations, nanochannel conductance deviated significantly from linearity and was seen to level off for the APTMS treated nanochannels. At pH 7.2, the amino groups may be expected to be positively charged.

Assuming that the conducting ions are Cl⁻ with a mobility of $7.9 \times 10^{-8}$ m²/(V s), the estimated surface charge is approximately 8 mC/m². In this case, σ/eh corresponds to about 5 mM, which is much larger than the bulk concentration of ~150 μM and hence σ/eh>>n. Treatment with NHS-SS-biotin drastically lowered conductance at low buffer concentrations, presumably due to reaction of the amino group with the NHS group resulting in a moiety with no charge. In this case, surface charge was lowered to such an extent that and σ/eh is comparable to n and the calculated predictions of conduction are not valid. However, since conductance decreases monotonically with bulk concentration, the equations put an upper bound of about 1 mC/m² on the surface charge.

Further treatment with NHS did not result in a large change in conductance. To clearly illustrate charge-governed and geometry-governed regimes, conductance values at 10 3× and 10×PBS (~150 μM and 1.5 M NaCl) for the three surfaces are shown in FIG. 37B. It can be seen that functionalization of nanochannel surfaces with small molecules resulted in a large change in surface charge, detected at low buffer concentrations, while conductance values at high buffer concentration remained unchanged, indicating no change in nanochannel geometry.

EXAMPLE 2

To study the effect of biological binding reactions on nanochannel surfaces, 1 mg/mL Alexa Fluor 488 labeled streptavidin (Molecular Probes, Eugene, Oreg.) in 0.1×PBS was introduced into a test device configured as described in Example 1 for 10 hours at room temperature, followed by rinsing in buffer. To ensure that any observed changes were not due to effects external to nanochannels such as blocking of nanochannel inlets, another nonbiotinylated control device was prepared by treatment with APTMS followed by NHS and was similarly treated with streptavidin. Use of fluorescently labeled streptavidin enabled electrical measurement as well as direct optical confirmation of the presence or absence of streptavidin on nanochannel surfaces.

Figure 38A:
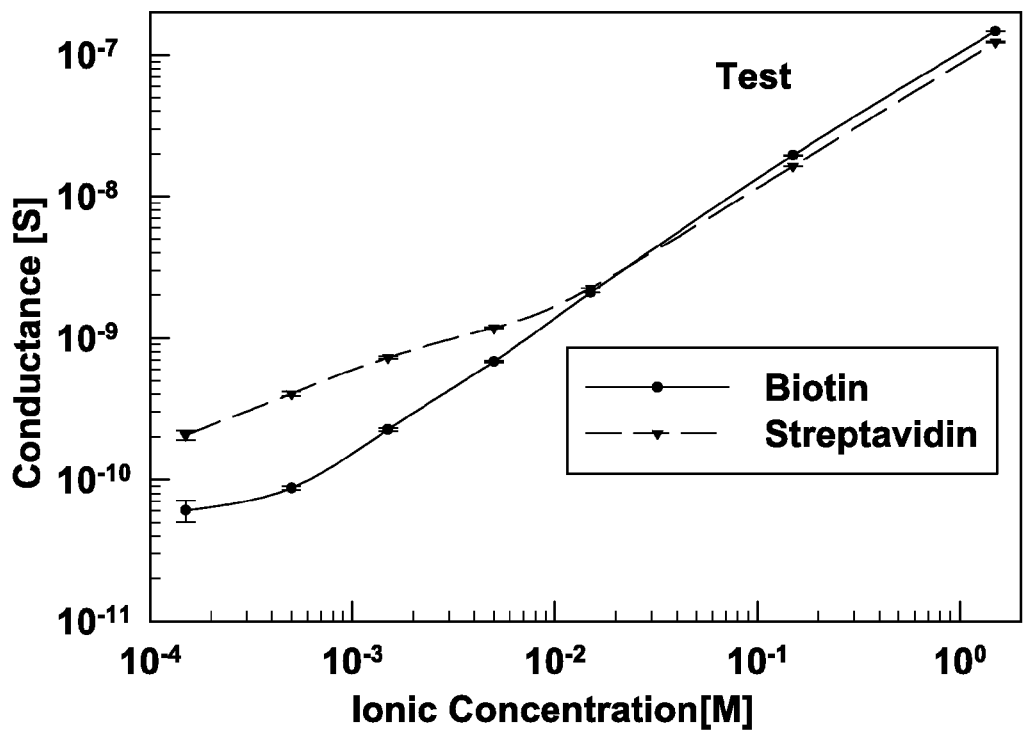
FIGS. 38A-38B are conductance measurements of the test device with a functionalized nanochannel and a control nanochannel over a range of ionic concentrations.
Figure 38B:
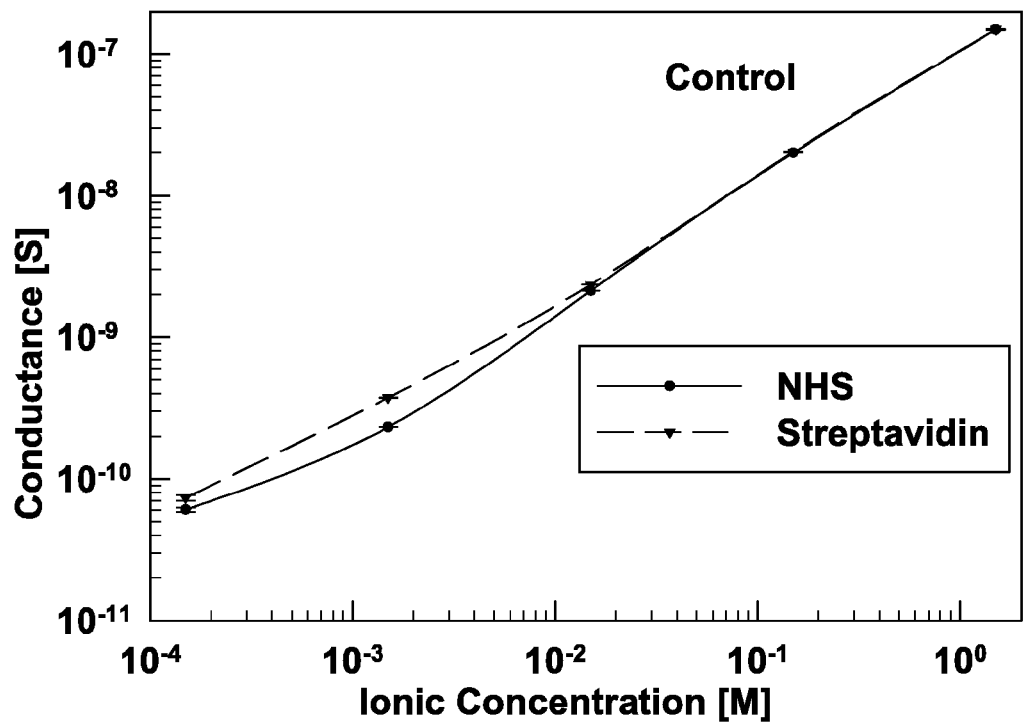

Referring now to FIGS. 38A and 38B, the conductance response of the test device functionalized with NHS-SS-biotin and passivated with NHS over a range of ionic concentrations is shown. The immobilized fluorescent streptavidin was imaged optically by fluorescence images obtained with a Nikon TE2000-U inverted epifluorescence microscope using an ORCA-ER (Hamamatsu Photonics Gmbh) camera to confirm the binding reaction.

Referring also to FIG. 38B, conductance measurements for the control device passivated completely with NHS can be seen. No fluorescent signal was observed in this case indicating that streptavidin did not get immobilized on the surface (inset). PBS buffer was used for the measurements.

Accordingly, conductance measurements revealed large changes in conductance of the biotinylated nanochannels (test device) in FIG. 38A at both low and high ion concentrations, but little change in conductance of the nonbiotinylated nanochannels (control device) as seen in FIG. 38B. Further, this is corroborated by, which clearly showed immobilization of streptavidin in the test device but not in the control device.

Figure 39:
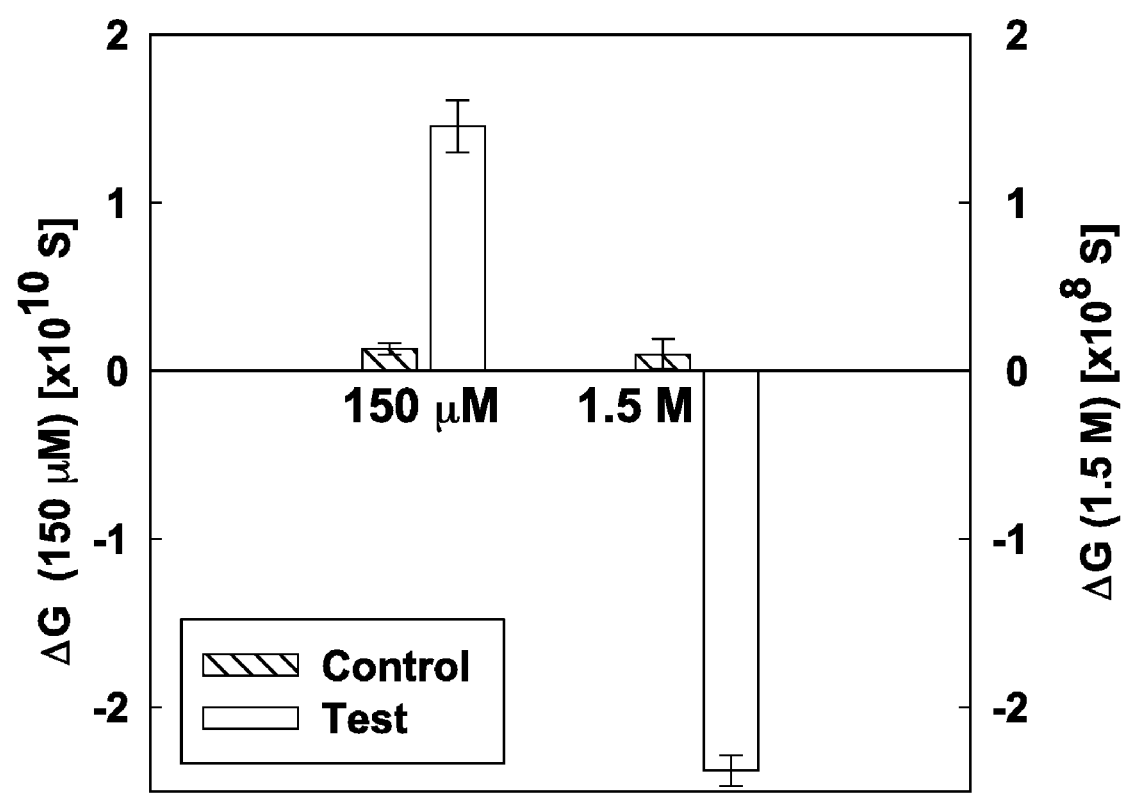
FIG. 39 is a graph showing changes in nanochannel conductance at low and high ionic concentrations according to an aspect of the present invention.

Conductance measurements in charge-governed and geometry-governed regimes shown in FIG. 39 reveal that immobilization of streptavidin in the nanochannels resulted in changing not only the surface charge but also the device geometry. At 10×PBS, conductance of the biotinylated nanochannels dropped by about 15% when streptavidin was introduced, indicating an effective reduction in channel size from about 30 to 25 nm or an immobilized layer effectively 2.5 nm thick on the surface. This change is consistent with the globular size of streptavidin (5-6 nm) and the change in size of colloids on protein binding reported in other studies. At low ion concentrations, conductance of the biotinylated nanochannels showed an increase, which implies an increase in the surface charge due to immobilization of streptavidin. Streptavidin with a mildly acidic pI of 5 is reported to have about two electron charges at pH 7.2, which qualitatively explains the increase in conductance. The conductance of the non-biotinylated nanochannels remained relatively unchanged, indicating that the changes observed in the test device can be attributed to the streptavidin binding reaction.

It can be seen that the biological binding events modulate surface charge and create a change in the nanochannel geometry. Moreover, conductance values were highly repeatable even after rinsing with different buffer concentrations. At the lowest buffer concentration, APTMS-treated surfaces showed the largest variability in conductance. This variability may be due to the presence of bivalent phosphate counterions in PBS, since multivalent ions are known to adsorb and sometimes even reverse charge on highly charged surfaces. In contrast, NHS and NHS-SS-biotin treated surfaces were extremely stable after rinsing with different buffer concentrations; conductance varied by less than $10^{-11}$ S in some cases. Assuming that change in conductance is roughly equivalent to a change in ionic concentration of Δσ/eh, it corresponds to variations in surface charge of approximately 0.1 mC/m² or one electron charge per 400 Å×400 Å area. This observation suggests that electrochemically stable nanochannel surfaces can be used as highly sensitive probes for measuring changes in surface charge. At high ionic concentrations, a variation of about 1% in nanochannel conductance was observed. This could be due to slight variations in concentration and temperature since the viscosity of water changes by 2% per 1° C. change in temperature in the 20-30° C. range, resulting in changes in ionic mobilities and conductance. Since the room temperature remained at 23±0.5° C. during the course of the experiment, these variations are not expected to materially affect the results. Another aspect of streptavidin immobilized on nanochannel surfaces is the deviation of conductance at low concentrations from that of nanochannels with a constant surface charge. This behavior could arise from a number of effects including charge regulation of streptavidin due to changes in pH, discreteness of charge, adsorption of ions, nonplanar geometry due to streptavidin, etc.

These experiments indicate that biomolecule charge and volume have opposite effects on nanochannel conductance: biomolecule charge increases the number of conducting ions in the nanochannel whereas volume exclusion of ions decreases the number of conducting ions. This is observed even when the nanochannel has a comparatively low surface charge to begin with, as in the present case. These experiments demonstrate that the ionic conductance of nanochannels reflects an interplay between the competing effects of biomolecule charge and size.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present disclosure and claims. Moreover, it is not necessary for a device or method to address each and every problem sought to be solved by the present invention, for it to be encompassed by the present disclosure and claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A nanofluidic device, comprising:
   at least a first and second fluid supply structure configured for supplying a fluid containing chemical or bio-chemical species;
   a nanotube of inorganic material which fluidly couples said at least first fluid supply structure to said second fluid supply structure;
   at least a first and second electrode, separated from one another along the length of said nanotube, and configured for establishing electrical contact with the fluid in said nanotube; and
   means for detecting the motion of the chemical or biochemical species flowing through said nanotube in response to current flow between said first and second electrodes;
   a gate electrode configured for controlling the flow of ions between said at least first and second fluid supply structure in response to the voltage applied to said gate electrode;
   wherein said gate electrode is retained proximal said inorganic nanotube; and
   wherein said nanofluidic device operates as a metal-oxide-solution field-effect transistor (FET).

2. A nanofluidic device as recited in claim 1, wherein said fluid supply structure comprises a nanofluidic channel structure.

3. A nanofluidic device as recited in claim 1, wherein said means for detecting is configured for detecting a change of current passing through said nanotube between said first and second electrode.

4. A nanofluidic device as recited in claim 1, wherein said means for detecting, comprises:
   a voltage source configured for establishing a biasing current between said first and second electrode, said biasing current passing through said fluid which comprises an ionic solution containing molecules to be detected; and
   a current detection circuit configured for registering transient changes in the biasing current in response to the translocation of the molecules through said nanotube.

5. A nanofluidic sensor, comprising:
   a nanofluidic system configured for receiving DNA molecules retained within a fluid;
   an inorganic nanotube coupled to said nanofluidic system through which the DNA molecules can be passed;
   at least a first and second electrode positioned proximal said inorganic nanotube and separated from one another;
   said electrodes configured for establishing electrical contact with the fluid which comprises an ionic solution;
   biasing source configured for establishing a bias current through the ionic solution between said first and second electrodes;
   a gate electrode disposed intermediate said nanotube on at least an exterior portion for controlling the flow of ions between said at least first electrode and at least said second electrode in response to the voltage applied to said gate electrode; and
   transient current detector configured for detecting transient changes in bias current levels through the fluid in response to the translocation of DNA molecules through the portion of the nanotube positioned between said first and second electrodes.

6. A nanofluidic sensor as recited in claim 5, wherein said fluid comprises an ionic solution of a known concentration.

7. A nanofluidic sensor as recited in claim 5, wherein said nanotube is configured to stretch the DNA molecule while it is passing through said nanotube.

8. A nanofluidic sensor as recited in claim 5, wherein said nanotube has a sufficiently high aspect ratio to confine the entire DNA molecule during translocation.

9. A nanofluidic sensor as recited in claim 5, wherein said nanofluidic system is configured with nanopores, nanochannels, or a combination of nanopores and nanochannels for supplying a fluid containing the DNA molecules to be passed through said nanotube.

10. A nanofluidic sensor as recited in claim 5, wherein said nanofluidic system comprises a nanopore structure.

11. A nanofluidic sensor as recited in claim 5, further comprising at least one access hole in said nanofluidic system through which the fluid is communicated to said nanotube.

12. A nanofluidic sensor as recited in claim 5, further comprising functionalizing of said nanotube to change its translocation characteristics.

13. A nanofluidic sensor as recited in claim 5, wherein said translocation of the DNA molecules is electrophoretically driven.

14. A nanofluidic transistor, comprising:
   a fluidic source;
   a fluidic drain;
   an inorganic nanotube coupled in fluidic communication between said fluidic source and fluidic drain; and
   a gate electrode retained proximal said inorganic nanotube for controlling the flow of ions between source and drain regions in response to the voltage applied to said gate electrode.

15. A transistor as recited in claim 14, wherein said nanofluidic transistor operates as a field-effect transistor (FET).

16. A transistor as recited in claim 14, wherein said nanofluidic transistor comprises a metal-oxide-solution field-effect transistor (MOSo/FET).

17. A transistor as recited in claim 14, wherein said transistor is configured to conduct either or both ionic polarities in response to voltage applied to said gate electrode.

18. A transistor as recited in claim 14, wherein said transistor comprises a p-type, n-type or ambipolar field effect transistor.

19. A transistor as recited in claim 14, wherein said transistor exhibits rapid field-effect modulation of ionic conductance.

20. A transistor as recited in claim 14, wherein the voltage applied to the gate electrode of said transistor shifts the electrostatic potential distribution within said nanotubes.

21. A transistor as recited in claim 14, wherein said inorganic nanotube comprises a silica material.

22. A transistor as recited in claim 14, wherein said nanotube is configured to have a diameter comparable with the diffuse layer of the electrical double layer (EDL) that forms within the nanotube to screen surface potential which remains non-zero even at the center of the nanotube.

23. A transistor as recited in claim 14, wherein said nanotube is configured with a diameter of approximately 50 nm or less.

* * * * *